(12) United States Patent
Schuetz et al.

(10) Patent No.: US 10,500,328 B2
(45) Date of Patent: Dec. 10, 2019

(54) CERAMIC WHOLE BLOOD HOLLOW FIBER MEMBRANE FILTER MEDIUM AND USE THEREOF FOR SEPARATING BLOOD PLASMA/SERUM FROM WHOLE BLOOD

(71) Applicant: Mann+Hummel GMBH, Ludwigsburg (DE)

(72) Inventors: Steffen Schuetz, Bietigheim-Bissingen (DE); Heike Rupp, Stuttgart (DE); Tobias Woerz, Leutenbach (DE); Dagmar Winkler, Filderstadt (DE); Kathrin Woerz, Leutenbach (DE); Frank Ehlen, Neunkirchen (DE); Karlheinz Muenkel, Oberderdingen-Flehingen (DE); Joachim Stinzendoerfer, Speyer (DE)

(73) Assignee: MANN+HUMMEL GmbH, Ludwigsburg (DE)

( * ) Notice: Subject to any disclaimer, the term of this patent is extended or adjusted under 35 U.S.C. 154(b) by 50 days.

(21) Appl. No.: 14/967,860

(22) Filed: Dec. 14, 2015

(65) Prior Publication Data
US 2016/0096148 A1 Apr. 7, 2016

Related U.S. Application Data

(63) Continuation of application No. PCT/EP2014/063590, filed on Jun. 26, 2014.

(30) Foreign Application Priority Data

Jun. 27, 2013 (DE) .................. 10 2013 010 735

(51) Int. Cl.
*A61M 1/34* (2006.01)
*B01D 69/08* (2006.01)
(Continued)

(52) U.S. Cl.
CPC ............ *A61M 1/34* (2013.01); *A61M 1/3403* (2014.02); *A61M 1/3496* (2013.01); *B01D 63/02* (2013.01);
(Continued)

(58) Field of Classification Search
CPC ...... A61M 1/34; A61M 1/1006; A61M 1/101; A61M 1/1012; A61M 1/3621;
(Continued)

(56) References Cited

U.S. PATENT DOCUMENTS 5,053,048 A * 10/1991 Pinchuk .............. A61L 33/0029
128/DIG. 21
5,294,401 A * 3/1994 Hagiwara .......... B01D 67/0088
128/DIG. 3
(Continued)

FOREIGN PATENT DOCUMENTS

DE 10332116 B3 2/2005
EP 0785012 A1 * 7/1997
(Continued)

*Primary Examiner* — John Kim
(74) *Attorney, Agent, or Firm* — James Hasselbeck

(57) ABSTRACT

A whole blood hollow fiber membrane filter medium is provided with a ceramic material having pores of a pore size that ensures permeability to blood plasma or serum and its molecular components while blood cells are retained. The whole blood hollow fiber membrane filter medium is used for separating blood plasma from whole blood, wherein the blood plasma preferably shows no hemolysis.

43 Claims, 1 Drawing Sheet

Cross-flow filtration module as used in Examples 1, 3, 4 and 6 comprising a single whole blood hollow fiber membrane filter medium inside of a filter housing.

Hollow fiber membrane filter medium inside of a filter housing

(51) Int. Cl.
  *B01D 69/02* (2006.01)
  *B01D 67/00* (2006.01)
  *B01D 71/02* (2006.01)
  *G01N 33/49* (2006.01)
  *B01D 63/02* (2006.01)
  *B01D 71/42* (2006.01)
  *B01D 71/68* (2006.01)
  *B01D 71/70* (2006.01)
  *C08G 77/04* (2006.01)
  *C08L 83/00* (2006.01)
  *C08L 83/04* (2006.01)
  *C08G 77/00* (2006.01)

(52) U.S. Cl.
  CPC ....... *B01D 63/021* (2013.01); *B01D 67/0041* (2013.01); *B01D 67/0088* (2013.01); *B01D 67/0093* (2013.01); *B01D 69/02* (2013.01); *B01D 69/08* (2013.01); *B01D 69/081* (2013.01); *B01D 69/087* (2013.01); *B01D 71/024* (2013.01); *B01D 71/025* (2013.01); *B01D 71/027* (2013.01); *B01D 71/028* (2013.01); *B01D 71/42* (2013.01); *B01D 71/68* (2013.01); *B01D 71/70* (2013.01); *G01N 33/491* (2013.01); *A61M 2205/33* (2013.01); *A61M 2205/3306* (2013.01); *B01D 2325/02* (2013.01); *B01D 2325/04* (2013.01); *B01D 2325/14* (2013.01); *B01D 2325/20* (2013.01); *C08G 77/00* (2013.01); *C08G 77/04* (2013.01); *C08L 83/00* (2013.01); *C08L 83/04* (2013.01)

(58) Field of Classification Search
  CPC .............. A61M 1/3659; A61M 1/3679; A61M 2205/12; A61M 2205/8206; A61M 2209/088; A61M 1/16; A61M 1/3482; A61M 1/3496; A61M 1/3633; B01D 2325/02; B01D 2325/04; B01D 2325/14; B01D 2325/20; B01D 67/0041; B01D 67/0088; B01D 69/02; B01D 69/08; B01D 69/081; B01D 69/087; B01D 71/024; B01D 71/025; B01D 71/027; B01D 71/028; B01D 15/08; B01D 63/02; B01D 63/021; B01D 67/0093; B01D 71/26; B01D 71/34; B01D 71/40; B01D 71/42; B01D 71/56; B01D 71/68; B01D 71/70; G01N 33/491; G01N 33/4005; C08G 77/00; C08G 77/04; C08L 83/00; C08L 83/04

See application file for complete search history.

(56) References Cited

U.S. PATENT DOCUMENTS

| | | | | |
|---|---|---|---|---|
| 5,674,394 | A * | 10/1997 | Whitmore | A61M 1/3496 210/321.6 |
| 5,707,584 | A * | 1/1998 | Terpstra | B01D 67/0041 264/177.11 |
| 5,919,356 | A * | 7/1999 | Hood | B01D 61/18 210/136 |
| 5,979,669 | A * | 11/1999 | Kitajima | B01D 39/2017 210/247 |
| 6,214,232 | B1 | 4/2001 | Baurmeister | |
| 6,270,674 | B1 | 8/2001 | Baurmeister | |
| 6,881,361 | B1 * | 4/2005 | Schulze | B01D 67/0009 264/171.26 |
| 2006/0108288 | A1 * | 5/2006 | Oishi | A61M 1/3472 210/639 |
| 2006/0184112 | A1 * | 8/2006 | Horn | A61L 29/126 604/103.08 |
| 2012/0226258 | A1 | 9/2012 | Otto | |

FOREIGN PATENT DOCUMENTS

| | | |
|---|---|---|
| EP | 0985442 A2 | 3/2000 |
| WO | 2008016292 A1 | 2/2008 |

* cited by examiner

Reference solutions comprising different concentrations of hemoglobin for determining the degree of hemolysis in blood plasma samples (mg/dl):

Cross-flow filtration module as used in Examples 1, 3, 4 and 6 comprising a single whole blood hollow fiber membrane filter medium inside of a filter housing.

Hollow fiber membrane filter medium inside of a filter housing

CERAMIC WHOLE BLOOD HOLLOW FIBER MEMBRANE FILTER MEDIUM AND USE THEREOF FOR SEPARATING BLOOD PLASMA/SERUM FROM WHOLE BLOOD

CROSS-REFERENCE TO RELATED APPLICATIONS

This application is a continuation application of international application No. PCT/EP2014/063590 having an international filing date of 26 Jun. 2014 and designating the United States, the international application claiming a priority date of 27 Jun. 2013, based on prior filed German patent application No. 10 2013 010 735.0, the entire contents of the aforesaid international application and the aforesaid German patent application being incorporated herein by reference.

BACKGROUND OF INVENTION

The present invention relates to a whole blood hollow fiber membrane filter medium including a ceramic material having a pore size ensuring permeability to the liquid part of whole blood, preferably to blood plasma or serum and its molecular components, but retaining blood cells and further relates to the use of said whole blood hollow fiber membrane filter medium for separating blood plasma or serum from whole blood.

In medical technology, various kinds of blood and plasma/serum separation and treatment processes are known and state of the art. The most common method for separating blood cells from the liquid part of the blood is centrifugation.

In transfusion medicine, filters are used to remove leucocytes from transfusion blood and to remove blood clots and particles. Furthermore, artery filters are applied during surgeries, e.g. to remove blood clots, particles and gas bubbles. Plasmapheresis filters are used to clean or to substitute plasma from patients, which is poisoned by bacteria, viruses or further components, which are life-threatening, with artificial blood plasma or plasma from donors.

Moreover, microdevices are known for whole blood analysis, which are either based on test stripes or on lab-on-a-chip technology. When using these devices, only a few microliters of blood are required for the blood or plasma/serum analysis. The separation of plasma/serum from whole blood is usually performed by fluid mechanical effects like the wetting behavior of different surfaces or the application of microchannels. Although this method is very attractive concerning the quick obtainment of blood analysis results, the results from these analyses are restricted to a few test-specific components. These applications are unable to replace a plasma/serum based blood analysis with the existing sophisticated systems in labs and hospitals, which comprise the analysis of a plurality of blood components and which are able to give an overall picture of a patient's state of health. Furthermore, the task of separating blood cells from the liquid part of the blood is also not yet solved satisfactorily for microdevices.

In many countries, it is obligatory to withdraw a sufficient amount of blood from the patients to be able to store the obtained plasma/serum sample for some time to check the analysis result some time later with a so-called retain sample. Until now, the task of obtaining enough cell-free plasma/serum can however only be accomplished by centrifugation.

The centrifugation procedures, which are typically used for separating blood plasma/serum from whole blood, are not only cumbersome requiring large amounts of manual and mechanical handling, but are also time consuming, which is particularly disadvantageous in emergency medicine.

Blood plasma/serum analysers, which have a great capacity for plasma/serum samples, cannot operate at full capacity when a centrifugation process is applied upstream, which works batch-wise and represents the »bottleneck« in blood sample processing. This bottleneck problem could possibly be overcome with a continuous filtration process instead of a centrifugation process for plasma/serum generation. Such a continous system would allow a flexible analysis of the samples: Urgent samples from emergency patients could be processed with a higher priority without any need of interrupting a running centrifugation process.

It is a further advantage of a simple filtration process for whole blood separation that the whole blood separation into plasma/serum and blood cells can be performed directly after collecting the whole blood sample. This is especially advantageous for the quality of the subsequent blood analysis as the red blood cell stability decreases with increasing sample storage time. This can influence the plasma/serum composition when the plasma/serum separation is not performed immediately after the blood sample withdrawal, but with some time delay. This aspect becomes important in rural areas or developing countries when there is no centrifuge available for the plasma/serum separation and when the blood sample has to be transported for a long period of time and/or distance, sometimes even in a hot and/or humid environment.

A subsequent whole blood separation into plasma/serum can be advantageous for point-of-care testing devices, which are used to provide a quick blood analysis at/near the patient to get a quick blood analysis result outside of a clinical laboratory to make immediate decisions about patient care. Typically point-of-care testing is performed by non-laboratory personnel. A quick foregoing plasma filtration process facilitates the quick blood analysis and enables new operating conditions for point-of-care devices, since most of them work with whole blood or with the aforementioned microdevices which lead to a very small yield of plasma/serum volume. The whole blood separation process can also be integrated within the point-of-care device.

Therefore, whole blood filtration methods have been developed as an alternative measure for obtaining blood plasma/serum from whole blood. These plasma/serum filtration methods known in the art are however problematic in view of e.g. the blood cell concentration, the plasma/serum yield, the molecular adsorbance capacity, the extent of hemolysis, and the leakage of blood cells (erythrocytes, thrombocytes and leukocytes). Hemolysis is one of the important problems because the red blood cells, if ruptured, will alter the concentration of some plasma/serum analytes required for further testing and, in some cases, make an analysis using optical measurements techniques impossible due to the red color of the released hemoglobin. Moreover, the leakage of blood cells is problematic because the cells or even other particles can damage the blood plasma/serum analyzers as the sensitive capillaries and conduits can become plugged. Only (substantially) cell- and hemolysis-free plasma/serum can be used for a reliable blood analysis.

Hollow fiber membrane devices permitting separation of blood plasma from whole blood without the need for a centrifugation have been used for plasma exchange therapy (PET)/apheresis. In PET, the separated plasma is eliminated and the separated blood cells with replacement fluids are returned to the patient. This hollow fiber membrane technology offers an alternative to centrifugation and conventional filtration techniques for bioseparation.

U.S. Pat. No. 5,674,394 discloses a small-volume disposable filtration technology to separate blood plasma from whole blood. The system for preparing said plasma comprises a single use filter unit having two inlets in fluid communication with each other, an outlet, and a filtration membrane selectively permeable to blood plasma separating the inlet from the outlet. Manually operable, single use pumps are connected to the inlets. A flow path is defined along the membrane between the pumps, whereby whole blood can be repeatedly exchanged between the two pumps, past the membrane, to cause plasma to flow through the membrane and out of the outlet.

U.S. Pat. No. 5,919,356 discloses a device for sampling a fluid, preferably a body fluid such as blood, the device having filtration means for separating components of the fluid, a conduit directing flow of the fluid to be sampled from a source through the device, and sensing means which can detect the presence of a component in the fluid.

US 2003/0206828 discloses a portable hand-held blood sampling device having a self-filling capability, which includes a blood separation filter. The filter has a plurality of pores sized to permit passage of selected blood constituents such as blood plasma through the device. The filter is a hollow fiber filter, which extends within and along a length of the tube, the filter being sealed at the first end thereof proximal to the inlet end and in fluid communication with the outlet end at a second end thereof.

A need remains for filter media for separating blood plasma/serum from whole blood, which allow for an effective separation of blood plasma/serum from whole blood and which are suitable for use in a quick, safe and robust way to get a suitable amount of cell-free plasma/serum, without causing hemolysis. With this kind of filtration process a deterioration of the blood quality after the blood withdrawal from the patient or bad analysis results due to a time delay in a centrifugation process or due to transportation will be avoided as the blood cell separation can be performed immediately without a centrifuge in an emergency case or at the point of collection of the blood sample.

It is therefore an object of the present invention to provide a whole blood hollow fiber membrane filter medium for separating blood plasma/serum from whole blood, which is advantageous over the prior art, in particular regarding the problems of hemolysis and leakage of blood cells (erythrocytes, thrombocytes and leukocytes).

It is another object of the present invention to provide a whole blood hollow fiber membrane filter medium, which can be used for separating blood plasma/serum from a whole blood sample, e.g. by cross-flow filtration, wherein the separation of a sufficient amount of cell-free blood plasma/serum is possible with no or substantially no hemolysis.

Additionally, it is an object of the present invention to provide a whole blood hollow fiber membrane filter medium, which can be used for separating blood plasma/serum from a whole blood sample, wherein the material and the surface properties of the filter medium are chosen in such a manner that hemolysis due to the contact between the whole blood sample and the hollow fiber membrane filter medium is reduced or avoided. That means that negative effects like pH-shifts, osmotic changes or capillary effects caused by the porous membrane structure are reduced.

It is yet another object of the present invention to provide a whole blood hollow fiber membrane filter medium, which can be used for separating blood plasma/serum from a whole blood sample, wherein the separation of blood plasma/serum is possible, preferably in a manual way or in an easy automatic way without using centrifugation means.

It is another object of the present invention to provide a whole blood hollow fiber membrane filter medium, which can be used for separating blood plasma/serum from a whole blood sample, wherein the separation is less time consuming than the separation with conventional methods such as centrifugation methods.

It is another object of the present invention to provide a whole blood hollow fiber membrane filter medium, which can be used for separating blood plasma/serum from a whole blood sample. It should be noted in this regard that there is typically no need that the blood cells are recovered so that the whole blood hollow fiber membrane filter medium containing the blood cells can be used as a medical disposable.

It is another object of the present invention to provide a whole blood hollow fiber membrane filter medium, which can be used for separating blood plasma/serum from a whole blood sample, and which is suitable for multiple use.

It is another object of the present invention to provide a whole blood hollow fiber membrane filter medium, which can be used for separating blood plasma/serum from an urgent whole blood sample in an emergency case. Ideally, the cell separation can already take place at the scene of blood withdrawal. Subsequently the obtained plasma/serum sample can be immediately processed and can be directly delivered into the blood plasma/serum analyzer, e. g. a point-of-care testing device. The term emergency case comprises not only patient diagnosis in case of accidents, but also all blood treatment processes as they are provided by medical offices or patient control during surgeries in hospitals. In this regard, it is also an object to overcome the bottleneck problem of centrifugation and/or to avoid a falsification of the blood analysis due to a long treatment or transport of the unseparated whole blood sample.

It is another object of the present invention to provide a whole blood hollow fiber membrane filter medium, which can be used for separating blood plasma/serum from a whole blood sample without clogging of the filter medium.

It is another object of the present invention to provide a whole blood hollow fiber membrane filter medium, which can be used for separating blood plasma/serum from a whole blood sample, wherein the whole blood hollow fiber membrane filter medium does not induce rupture of blood cells e.g due to frictional forces or other mechanical stresses.

It is another object of the present invention to provide a whole blood hollow fiber membrane filter medium, which can be used for separating blood plasma/serum from a whole blood sample and reduces the risk of a leakage of red blood cells into the filtrate.

It is another object of the present invention to provide a whole blood hollow fiber membrane filter medium, which is suitable for providing a blood cell containing concentrate with which further testing is possible if desired.

It is another object of the present invention to provide a whole blood hollow fiber membrane filter medium which leads to a cell-free or substantially cell-free plasma/serum as a filtrate, wherein the relative amounts of the molecular components to be analyzed remain substantially unchanged upon filtration. Ideally, the whole blood hollow fiber membrane filter medium is inert and hemocompatible, releases no extractables or particles, and neither leads to the adsorption of particular blood plasma/serum components on its solid surface nor to a cross-reaction of particular blood plasma/serum components with its solid surface.

SUMMARY OF THE INVENTION

The above mentioned objects of the present invention are achieved by a whole blood hollow fiber membrane filter medium including a ceramic material having pores of a pore size ensuring permeability to blood plasma or serum, but retaining blood cells, i.e. all three kinds of blood cells (erythrocytes, thrombocytes and leukocytes). In order to allow subsequent blood plasma/serum analysis, the pore size ensures permeability to all molecular plasma/serum components. Plasma/serum components can be classified into different groups including electrolytes, lipid metabolism substances, markers, e.g. for infections or tumors, enzymes, substrates, proteins, and even pharmaceuticals and vitamins.

The pore structure may be defined e.g. by the median and average diameter of the pores, the pore size distribution, and the porosity of a material. Preferably, the properties of the whole blood hollow fiber membrane filter medium regarding the median diameter of the pores, the pore size distribution, and the porosity are selected in such a way that the filter medium is suitable for avoiding hemolysis and leakage of blood cells. Furthermore, the surface roughness of the whole blood hollow fiber membrane filter medium is preferably selected in such way that the blood cells are not ruptured by frictional forces. Moreover, it can be preferred that the whole blood hollow fiber membrane filter medium is modified in that it is e.g. pre-wetted or coated, in order to obtain certain wettability properties, hydrophilic/hydrophobic properties, oleophilic/oleophobic properties or a certain surface charge of the filter medium, which can be advantageous in terms of avoiding hemolysis and the leakage of blood cells.

The objects of the present invention are also achieved by the use of the whole blood hollow fiber membrane filter medium of the invention for separating blood plasma/serum from a whole blood sample. Preferably, the whole blood hollow fiber membrane filter medium of the invention is used for separating blood plasma/serum from a whole blood sample by cross-flow filtration to avoid clogging of the filter medium.

DESCRIPTION OF PREFERRED EMBODIMENTS

Figure 1:
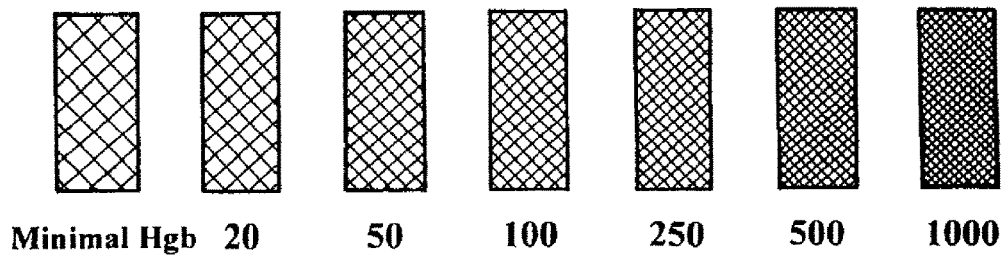
FIG. 1 shows reference solutions including different amounts of hemoglobin for determining the degree of hemolysis in blood plasma samples (see Jie Zhao, Quancheng Kan, Jianguo Wen, Yidong Li, Yunqiao Sheng, Li Yang, Jason Wu and Shengjun Zhang: *Hemolysis of Blood Samples has no Significant Impact on the Results of Pharmacokinetic Data. Bioequivalence & Bioavailability,* 2012).

As used herein, the term "whole blood" refers to blood composed of blood plasma, which is typically unclotted, and cellular components. The plasma represents about 50% to about 60% of the volume, and cellular components, i.e. erythrocytes (red blood cells, or RBCs), leucocytes (white blood cells, or WBCs), and thrombocytes (platelets), represent about 40% to about 50% of the volume. As used herein, the term "whole blood" may refer to whole blood of an animal, but preferably to whole blood of a human subject.

Erythrocytes constitute about 90% to about 99% to the total number of all blood cells and have the form of biconcave discs and measure about 7 μm in diameter with a thickness of about 2 μm in an undeformed state. During maturation in the bone marrow the erythrocytes lose their nucleus. They contain the plasma membrane protein spectrin and other proteins to provide flexibility to change shape as necessary. Their unique and flexible shape enables them to pass through very narrow capillaries and provides for maximum surface area to transfer oxygen and carbon dioxide. This flexibility makes it particularly difficult to separate the red blood cells from a whole blood sample by filtration as they can elongate themselves and reduce their diameter down to about 1.5 μm. Normal whole blood contains approximately 4.5 million to 5.5 million erythrocytes per microliter. The life-span of erythrocytes is approximately 120 days in the circulating bloodstream. One core component of erythrocytes is hemoglobin which binds oxygen for transport to the tissues, then releases oxygen, and binds carbon dioxide to be delivered to the lungs as waste product. Hemoglobin is responsible for the red color of the erythrocytes and therefore of the blood in total. Erythrocytes are the major factor contributing to blood viscosity.

Leucocytes make up less than about 1% of the total number of all blood cells and can be differentiated into different white blood cell groups (lymphocytes, granulocytes and monocytes). They can leave capillaries via diapedesis. Furthermore, they can move through tissue spaces by amoeboid motion and positive chemotaxis. They have a diameter of about 6 μm to about 20 μm. Leucocytes participate in the body's defense mechanisms e.g. against bacterial or viral invasion.

Thrombocytes are the smallest blood cells with a length of about 2 μm to about 4 μm and a thickness of about 0.9 μm to about 1.3 μm. They are membrane-bound cell fragments that contain enzymes and other substances important to clotting. In particular, they form a temporary platelet plug that helps to seal breaks in blood vessels.

The terms "blood plasma" or "plasma" refer to the liquid part of the blood and lymphatic fluid, which makes up about half of the volume of blood (e.g. about 50 vol.-% to about 60 vol.-%). Plasma is devoid of cells, and unlike serum, has not clotted. So it contains all coagulation factors, in particular fibrinogen. It is a clear yellowish liquid including about 90 vol.-% to about 95 vol.-% water.

The term "blood serum" or "serum" refers to the clear liquid that separates from blood when it is allowed to clot completely, and is therefore blood plasma from which in particular fibrinogen has been removed during clotting. Like plasma, serum is light yellow in color.

Molecular plasma/serum components can be classified into different groups including electrolytes, lipid metabolism substances, markers, e.g. for infections or tumors, enzymes, substrates, proteins, and even pharmaceuticals and vitamins.

As used herein, the term "cell-free" describes a plasma/serum sample with no or substantially no cells (erythrocytes, leucocytes, thrombocytes) in its volume that is prepared by e.g. a centrifuge. A substantially cell-free or cell-free sample is needed for a subsequent plasma/serum analysis to prevent blocking of the analysis system.

For the plasma analysis in the examples, the following analytes were chosen which comprise the relevant molecular groups. The reference concentration ranges of analytes for whole blood with heparin stabilization depend on the applied measurement technique. The following exemplary reference concentration ranges of analytes are obtained by the analysis device "Dimension" from Siemens.

| Plasma components | | Reference concentration ranges of analytes for whole blood with heparin stabilization and the chosen measurement device |
|---|---|---|
| Electrolytes | Potassium | 3.5-5.1 mmol/l |
| | Sodium | 136-145 mmol/l |
| | Calcium | 2.12-2.52 mmol/l |
| | Magnesium | 0.74-0.99 mmol/l |
| | Chloride | 98-107 mmol/l |
| | Phosphate | 0.80-1.60 mmol/l |
| Lipids | Triglycerides | 75-175 mg/dl |
| | Cholesterol | 110-200 mg/dl |
| | HDL-cholesterol | 35-60 mg/dl |
| | LDL-cholesterol | <150 mg/dl |
| Infection markers | CRP | 0-5.00 mg/l |
| Enzymes | AST/GOT | 0-35 Unit/l |
| | Lipase | 114-286 Unit/l |
| Substrates | Albumin | 3.4-5.0 g/dl |
| | Bilirubin | 0-1.0 mg/dl |
| | Glucose | 74-106 mg/dl |
| | Creatinine | 0.60-1.30 mg/dl |
| Proteins | IgG | 6.81-16.48 g/l |
| | Ferritine | 3.0-244 ng/l |

The analysis device "Dimension" from Siemens may not only be used for the analysis of blood plasma, but also for the analysis of blood serum.

As used herein, the expression "ensuring permeability to blood plasma or serum" preferably means that none of the above mentioned plasma or serum components to be analyzed is retained completely upon filtration. Preferably, the concentrations of the plasma or serum components to be analyzed are not significantly changed compared to the whole blood sample upon filtration. More preferably, the concentrations of the plasma or serum components to be analyzed are changed by not more than about 50%, preferably by not more than about 35%, more preferably by not more than about 10%, most preferably by not more than about 8%.

As used herein, the term "hemolysis" refers to the rupture of erythrocytes, e.g. due to chemical, thermal or mechanical influences, causing the release of the hemoglobin and other internal components into the surrounding fluid. Hemolysis can be visually detected by showing a pink to red tinge in the plasma/serum. Hemolysis is a common occurrence seen in serum and plasma samples and may compromise the laboratory's test parameters for blood analysis. Hemolysis can originate from two sources. In vivo hemolysis may be due to pathological conditions such as autoimmune hemolytic anemia or transfusion reaction. In vitro hemolysis may be due to improper specimen sample collection, specimen sample processing or specimen sample transport. In particular, hemolysis may be caused by a high pressure drop and high shear or elongation rate, which may e.g. occur during filtration processes when the sample is passed through a porous filter medium. Other important factors for hemolysis are bacterial contamination, pressure, temperature, osmotic environment, pH value, contact with surfaces, frictional forces, blood age and storage time of the unseparated whole blood sample.

The degree of hemolysis can be detected visually in comparison to a plasma reference solution having a certain concentration of hemoglobin (Hb, Hgb) (see e.g. FIG. 1). Blood plasma samples having the same color as a reference solution including no hemoglobin show no hemolysis (samples are classified as "o"). Blood plasma samples being equally or less red than a solution including about 50 mg/dl hemoglobin show substantially no hemolysis (samples are classified as "n"). In this respect, "substantially no hemolysis" means that the blood plasma samples show such a degree of hemolysis that is still sufficiently low to ensure that the samples can be analyzed with satisfactory results, e.g. by the plasma analysis device "Dimension" from Siemens. Blood plasma samples being equally or less red than a solution including about 100 mg/dl hemoglobin show a medium degree of hemolysis (samples are classified as "m"). Blood plasma samples with a color corresponding to a solution with a higher hemoglobin content than 100 mg/dl show a high degree of hemolysis (samples are classified as "h"). Reference solutions including 20, 50, 100, 250, 300 and 1000 mg/dl are provided in FIG. 1.

For the filtration of whole blood, there are in principal different filtration processes available. Based on process technology, filtration processes are subdivided into three different operational modes:

Dead-end filtration as a static operational mode
Cross-flow filtration as a dynamic operational mode
Submerged filtration systems In the dead-end operational mode, the feed flux is typically orthogonal to the surface of the hollow fiber membrane filter medium and the hollow fiber membrane filter medium is flowed through typically orthogonally by the filtrate so that a dead-end module is operated as a two-end module. All particles to be retained are deposited on the membrane surface. The so-called cover layer leads to a time-dependent, increasing flow resistance and the permeate flux through the membrane is reduced over time, typically in a constant pressure operational mode. After a certain filtration time-interval the module has to be flushed to remove the cover layer. Typically dead-end filtration is a discontinuous process.

In the cross-flow filtration mode, there is typically a flux parallel to the surface of the hollow fiber membrane filter medium on the feed side. Also in the cross-flow mode, the particles to be separated are deposited on the membrane surface and build up a cover layer. With the feed flux parallel to the cover layer, there is a control mechanism for the cover layer formation. Cross-flow shear forces are induced at the membrane surface, which can transport deposited particles from the cover layer to the feed flux. The cover layer can become steady state if there is a balance between particle deposition and particle re-entrainment. If the pressure drop of the cover layer increases, a constant or pulsating back-flushing with the filtration permeate is applied to remove the cover layer.

Thus, the term "cross-flow filtration" as used herein refers to a filtration process, wherein a feed stream tangentially passes across the surface of a hollow fiber membrane filter medium or another type of filter medium, and two exiting streams are generated. The permeate or filtrate stream is the portion of the fluid that passes through the filter medium. This permeate or filtrate should contain the same percentage of soluble and/or insoluble components as the initial feed stream, provided these components are smaller than the pore size of the filter medium. The retentate stream is the remainder of the feed stream, which does not pass through the filter medium, but may continue to flow across the filter medium, thereby "cleaning" and thickening. This "cleaning" is to be understood in that the use of a tangential flow will prevent thicker particles from clogging the membrane as observed, for example, in filter cakes in dead-end filtration processes. The filtrate volume can be increased by repeatedly passing the retentate across the filter medium. Besides the pulsating flow from one side of the filter housing to the other, a circuit operation mode is, in principal, also possible.

In principal, "cross-flow filtration" is highly advantageous for the purpose of the present invention, i.e. whole blood filtration, because it is particularly suitable for the pressure and shear force sensitive blood cells. Especially erythrocytes are very sensitive concerning static pressure drop which leads to cell deformation. The application of a cross-flow current along a membrane keeps the cells in movement within the liquid phase and away from the membrane surface so that it is possible to perform the filtration with an elevated transmembrane pressure at a simultaneously reduced risk of hemolysis because a high transmembrane pressure as well as plugging of the filter medium due to a high cell amount can effectively be avoided. To gain the plasma/serum for further analysis or storage, the whole blood samples to be filtered by means of cross-flow filtration typically have a volume of from about 0.01 ml to about 10 ml.

As used herein, "outside-in" or "out-in" cross-flow filtration describes an operating mode of filter media of tubular or capillary shape, e.g. hollow fiber membrane filter media. In this operating mode, the feed stream flows outside and between the filter medium in the shell side of the filter module and the filtrate penetrates through the filter medium wall to the inside. The retention typically takes place at the outer surface of the filter medium and sometimes to a low degree within the filter medium itself.

Figure 2:
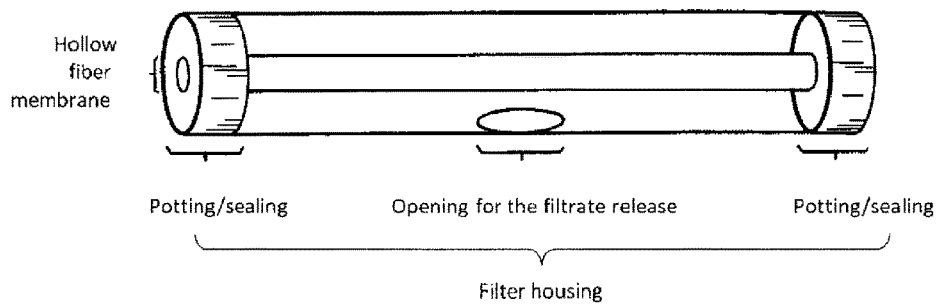
FIG. 2 shows a cross-flow filtration module as used in Examples 1, 3, 4, 6 and 8 including a single whole blood hollow fiber membrane filter medium inside a filter housing.

As used herein, "inside-out" or "in-out" cross-flow filtration describes the opposite operating mode of the hollow fiber membrane filter medium compared to the "out-in" operating mode. The feed flows inside the filter medium and the filtrate penetrates through the filter medium wall to the outside. The retention typically takes place at the inner surface of the tubular filter medium and sometimes to a low degree within the filter medium itself. An exemplary in-out cross-flow filtration module is shown in FIG. 2.

The out-in configuration provides more flexibility in the amount of feed to flow around the hollow fiber membrane filter medium, whereas the in-out configuration offers a much more defined and homogeneous flow distribution through the bore of the hollow fiber membrane filter medium compared to the out-in configuration. The in-out arrangement is close to a bionic principle: Blood flow in narrow capillaries tends to produce an almost cell-free boundary plasma layer adjacent to the vessel wall as the blood cells arrange themselves in the middle of the blood flow where the flow velocity is highest. It is believed that this cell distribution facilitates the filtration as this cell distribution reduces the risk of pore plugging and subsequent hemolysis.

As used herein, the term "hollow fiber membrane filter medium" refers to a membrane filter medium preferably of tubular or capillary shape, which is preferably suitable for use in cross-flow filtration, more preferably for use in the in-out filtration mode. Dead-end filtration is also possible with an in-out filtration mode. Cross-flow filtration is preferred according to the present invention, however. Similarly, with an out-in filtration mode, cross-flow and dead-end filtration are also possible, wherein cross-flow filtration is also preferred. Such hollow fiber membrane filter media may be prepared by a technique referred to as phase inversion. Phase inversion can be achieved by solvent evaporation, non-solvent precipitation and thermal gelation. In principal, phase separation processes can e.g. be applied to a large number of polymers but also to glasses and metal alloys. However, said process may also be applied to ceramic materials.

Ceramic hollow fiber membrane filter media can principally be prepared by a phase inversion process as described in the following.

A viscous spinning dope including at least one ceramic powder material (primary powder), at least one polymer, and at least one solvent, and optionally a dispersing agent, a polymer additive and/or a sintering aid, is prepared by milling and stirring. It is preferred that the polymer is soluble in the solvent. Preferred polymers in this regard are e.g. polyacrylonitrile or polyethersulfone; a preferred solvent is e.g. n-methyl-pyrrolidone. The at least one ceramic powder material preferably comprises aluminum oxide as main component. The amount of the polymer based on the total weight of the spinning dope is from about 1 weight % to about 50 weight %, the amount of the solvent based on the total weight of the spinning dope is from about 10 weight % to about 90 weight %, the amount of the ceramic powder material based on the total weight of the spinning dope is from about 3 weight % to about 50 weight %. The at least one ceramic powder material preferably has a volumetric median particle diameter from about 0.1 µm to about 2.0 µm, preferably from about 0.1 µm to about 1.5 µm. Typically, further additive components are homogenized with the spinning dope, e.g. dispersant agents, polymer additives, sintering aids and others. These further additive components are typically used in amounts of up to about 5 weight % based on the total weight of the spinning dope.

After homogenization, the spinning dope is conducted through the annulus cross-section of a multi-component nozzle, giving the hollow fiber structure to the ceramic hollow fiber membrane filter material. The bore fluid is conducted through the nozzle through the bore volume along the nozzle axis. The spinning velocity of the spinning dope is preferably from about 0.5 m/min to about 15 m/min. The fluid velocity of the bore fluid is preferably from about 0.06 m/min to about 60 m/min. This refers to volume flow rates of typically from about 0.01 liters/h to about 5 liters/h for the spinning dope and typically from about 0.007 liters/h to about 2.8 liters/h for the bore fluid. The spinning process is performed within an ambient temperature range from about 10° C. to about 40° C., preferably from about 18° C. to about 30° C. The overpressure imposed on the spinning dope in front of the spinning nozzle is preferably lower than 10 bar. In a more preferable operation mode, it is lower than 6 bar.

When the spinning dope contacts the non-solvent, typically aqueous precipitation bath and the bore fluid at the nozzle orifice, the solvent within the spinning dope is removed by water and the spinning dope solidifies (phase inversion) as the polymer is not soluble in the precipitation bath. Typically, the bore fluid has the same composition as the precipitation bath fluid into which the spinning dope is conducted. By the contact of the spinning dope with the bore fluid and the precipitation bath, an inner and an outer precipitation process is initiated at the inner and the outer surface of the hollow fiber. Dependent on the solvent content of the precipitation bath and the bore fluid and dependent on additives, the temperature and the viscosity of the precipitation bath and the bore fluid, the diffusion process, which controls the formation of the porous membrane structure during precipitation, is influenced. With a high diffusion velocity, a finger pore structure is generated, with low diffusion velocities, a sponge membrane structure is generated.

The spinning dope is usually directly conducted into the precipitation bath when the orifice of the spinning nozzle is dipped into the precipitation bath. In another preferred spinning process design an air gap with a maximum length of 10 cm is adjusted between the orifice of the spinning nozzle and the surface of the precipitation bath. Preferably, the water used in the precipitation bath and in the bore fluid is ion-free water produced by reverse osmosis to prevent plasma/serum falsification of the permeate during filtration by retained ions from the hollow fiber membrane filter medium production.

The solidified polymer pre-defines the hollow fiber membrane filter medium structure. The resulting green fiber is deposited within the precipitation bath and remaining solvent molecules are washed out. The resulting green fiber is then dried at a temperature of from about 40° C. to about 90° C. for a time interval of from about 1 hour to about 24 hours. Then the fiber is heated and kept at a temperature from about 200° C. to about 600° C. During this period the polymer is burned out, i.e. removed from the fiber. Then the fiber is further heated up and kept at a temperature from about 1,000° C. to about 2,000° C., preferably from about 1,350° C. to about 1,700° C., for a time interval from about at least 1.0 hour, preferably for a time interval from 1.5 to 12 hours, and the ceramic material is sintered. The final ceramic hollow fiber membrane filter medium structure is generated during this sintering process. This process produces a single layer ceramic hollow fiber membrane filter medium which can be subject to further surface modification, e.g. by coating or by pre-treating, e.g. pre-wetting, it.

From the precipitation step until the end of the sintering step, there is typically a thermal shrinkage of the fiber diameter. This shrinkage is from about 5% to about 30% relative to the initial fiber diameter after the precipitation step.

The basic concept of this process as well as the physical and technical principles for the generation of ceramic hollow fiber filter media are described in the granted patent DE 199 10 012 C1. Some basic differences between the present process of the inventors and the process as described in the patent DE 199 10 012 C1 arise. The patent DE 199 10 012 C1 describes a process in which two polymer solutions are used to produce a multi-layer material, whereas in the process of the inventors only one polymer solution containing the ceramic powder material is used to produce a single-layer hollow fiber membrane filter medium. Furthermore, the patent DE 199 10 012 C1 describes a process in which polysaccharides, derivatives of polysaccharides or polyvinyl alcohol are used as polymers, whereas in the process of the inventors polyacrylonitrile or polyethersulfone is used. Furthermore, the patent DE 199 10 012 C1 describes a process in which amine-n-oxide is used as a solvent, whereas in the process of the inventors e.g. n-methyl-pyrrolidone is used as a solvent for the preparation of the spinning dope.

The production of hollow fiber membrane filter media by phase inversion is also described in patent application DE 101 48 768 A1 filed by the present applicant.

Alternatively, the ceramic hollow fiber membrane filter medium can be produced by a high-pressure extrusion process also based on fiber generation by phase inversion. In this case, the spinning dope is pressed through a hole perforation plate instead of a multicomponent nozzle. The hole perforation plate is also designed with multi-component openings. The string of the spinning dope is conducted into a precipitation bath and the spinning dope solidifies in the geometry of the green fiber as described before. The pressure which is imposed on the spinning dope in front of the hole perforation plate is at least 20 bar.

Alternatively, the ceramic hollow fiber membrane filter medium can be produced by a high-pressure extrusion process that is not using the phase inversion effect. In this case, the fibers are extruded directly from a viscous polymer melt or solution and dried and sintered directly after the extrusion process. This method for the production of ceramic hollow fiber membranes is described in the patent applications WO 94/23829 and WO 2008/016292 A1.

After their preparation, the ceramic hollow fiber membrane filter media should be handled with gloves to prevent contamination with the lipids of skin.

As used herein, the term "ceramic material" refers to an inorganic material made from compounds of a metal and a non metal. Ceramic materials may be crystalline or partly crystalline or amorphous. Typically, the "ceramic material" is made from a "ceramic powder material". In particular, it may be formed from a suspension of the ceramic powder material (here the spinning dope) to give the green body (here the green fiber). The shape of the green body is stabilized by the action of heat (heating up and sintering) and subsequent cooling.

Technical ceramic materials can also be classified into the following distinct material categories:
    oxides: such as alumina, beryllia, ceria, zirconia, titania, silica, yttrium oxide,
    nonoxides: such as carbide, boride, nitride, silicide,
    composite materials: such as particulate reinforced, fiber reinforced, combinations of oxides and nonoxides, and
    further material composites: such as zeolites, perovskite and the like.

According to the present invention, the ceramic material preferably comprises a metal oxide, which may be selected from the group consisting of aluminum oxide, silicon oxide, titanium oxide, yttrium oxide, zirconium oxide. Preferably, the ceramic material mainly comprises aluminum oxide, optionally in combination with another metal oxide, e. g. titanium dioxide. It is particularly preferred that the ceramic material comprises aluminum oxide in an amount of at least about 98 wt.-%, preferably in an amount of about 99 wt.-%, more preferably in an amount of from about 99.5 wt.-% to about 99.9 wt.-%, and optionally further metal oxides in an amount of from about 0 wt.-% to about 2 wt.-%, preferably from about 0.1 wt.-% to about 1 wt.-%, more preferably from about 0.1 wt.-% to about 0.5 wt.-% based on the total weight of the ceramic material.

As used herein "aluminum oxide" (alumina, $Al_2O_3$) is contained in the ceramic material as alpha-alumina ($\alpha$-$Al_2O_3$) or gamma-alumina ($\gamma$-$Al_2O_3$). Preferably, the volumetric median particle diameter of the aluminum oxide powders used for making the ceramic material is from about 0.1 µm to about 2.0 µm.

For hollow fiber membrane filter media, the pore size is an important characteristic for achieving a desired separation of components from a sample, such as the separation of blood plasma/serum from a whole blood sample. The pore size may be defined by the size of the molecules which are retained (molecular weight cut-off, MWCO). Alternatively, the pore size may be defined by the number-related or volume related median diameter of the pores, preferably by the volume related median diameter of the pores (median pore diameter).

Another important parameter in this regard is the volumetric pore size distribution (pore size distribution). Still further, other measures to describe the pore structure, such as the accessible porosity may be used.

The MWCO is defined as the molecular weight solute (in Daltons, Da) in which 90%, preferably 95%, more preferably 99%, of the solute is retained by the membrane, or the molecular weight of the molecule (e.g. globular protein) that is retained to 90%, preferably 95%, more preferably 99%, by the membrane.

The median pore diameter and the pore size distribution can be determined by mercury intrusion porosimetry. In mercury intrusion porosimetry, gas is evacuated from the sample cell, and mercury is then transferred into the sample cell under vacuum and pressure is applied to force mercury into the sample. During measurement, applied pressure (p) and intruded volume of mercury (V) are registered. As a result of analysis, an intrusion-extrusion curve is obtained. Parameters describing the pore structure of the sample can be calculated from the data obtained. The principle of this technique is based on the fact that mercury does not wet most substances and, therefore, will not penetrate pores by capillary action, unless it is forced to do so. Liquid mercury has a high surface tension ($\gamma$) and also exhibits a high contact angle ($\theta$) against most solids. Entry into pore spaces requires applying pressure (p) in inverse proportion to the pore radius (r). Based on these known parameters, the pore radius can be determined by the Washburn equation (Washburn 1921):

$$p \times r = -2 \times \gamma \times \cos\theta$$

wherein r is the radius of the pore where mercury intrudes, $\gamma$ is the surface tension of mercury and $\theta$ is the contact angle of the mercury on the surface of a solid sample. Generally used values for the surface tension and the contact angle of mercury are 480 mNm$^{-1}$ and 140°, respectively. According to the Washburn equation, the radius of the pores can therefore be calculated from the applied pressure.

The measurements for the mercury intrusion porosimetry are performed according to DIN 66133.

The total pore volume ($V_{tot}$) is the total intruded volume of mercury at the highest pressure determined. The total pore surface area (S), which is also often referred to as specific pore surface area, is calculated by the following equation:

$$S = \frac{1}{\gamma|\cos\theta|} \int_0^{V_{tot}} p \, dV$$

The total pore surface area (S) is the area above the intrusion curve.

The mean pore diameter ($d_{mean}$), which is also often referred to as average pore diameter or hydraulic diameter, is calculated by the following equation $$d_{mean} = 4 \cdot \frac{V_{tot}}{S}$$

based on an assumption of cylindrical shape of pores open at ends.

The median pore diameter ($d_{median}$) is the pore diameter at which 50% of the total intruded volume of mercury has intruded into the sample. In general, the mean pore diameter rather emphasizes the smaller pores more than the median pore diameter.

The volumetric pore size distribution curve is characterized by three values of the cumulative residue curve: D10 (10% of the pore volume consists of pores with a bigger diameter than D10), D50 (median pore diameter $d_{median}$, 50% of the pore volume consists of pores with a bigger diameter than D50) and D90 (90% of the pore volume consists of pores with a bigger diameter than D90). The closer the values for D10 and D90 are together, the narrower is the pore size distribution, indicated by a value for the ratio of D10/D90, which is close to 1.

In addition, mercury intrusion porosimetry can provide the accessible porosity of a material. Porosity is a measure of the void (i.e. "empty") spaces in a material, and is a fraction of the volume of voids over the total volume, between 0-1, or as a percentage between 0%-100%. Accessible porosity refers to the fraction of the total volume, in which fluid flow is effectively taking place, and includes open pores, in particular dead end pores, but excludes closed pores.

Fully automated mercury porosimeters for the determination of volume pore size distribution, median pore diameter, total pore volume and specific pore surface are commercially available e.g. from Porotec GmbH. Different instruments and options allow the possibility to determine pore radii from 3,000 micron to 1.8 nm.

In terms of hemolysis upon whole blood filtration, the surface roughness of the ceramic material is a further characteristic of the hollow fiber membrane filter media.

The surface roughness of a hollow fiber membrane filter medium including aluminum oxide ($Al_2O_3$) as ceramic material depends on the preparation method and is related to many factors, such as the $Al_2O_3$ content in the spinning suspension, the volumetric median particle diameter of the $Al_2O_3$ powder, the sintering temperature, the sintering time, among others. In general, hollow fiber membrane filter media fabricated from a low $Al_2O_3$ content in the spinning suspension, a smaller particle size in the primary powder, a higher sintering temperature and a longer sintering time show a smoother surface. In this regard, it should also be mentioned that hollow fiber membrane filter media prepared from spinning suspensions containing a primary powder with a volumetric median pore diameter of 0.01 or 0.3 µm have shown a smoother outside surface compared to hollow fiber membrane filter media prepared using the spinning suspensions containing only 1 µm particles (see Kang Li: *Ceramic Membranes for Separation and Reaction*. John Wiley & Sons, Ltd., 2007).

If the surface of a hollow fiber membrane filter medium is smooth, less hemolysis occurs upon blood filtration because erythrocytes are less easily ruptured due to shear forces caused by the surface roughness.

The surface roughness can be determined by optical measurement methods, e.g. by the µSurf device working with a CMP technology (confocal-multi-pinhole) from NanoFocus. With this contact-free measurement technique it is possible to analyze three-dimensional micro- and nano-structures and evaluate the surface quality according to standards, especially to ISO 25178. A characteristic parameter is Sa, the arithmetical mean height of the surface within a definition area. An advantage of the optical measurement system is that even the roughness of the inner surface of a hollow fiber membrane can be analyzed. The influence of the curvature of the surface on the measuring result can be computationally eliminated.

Furthermore, it is advantageous in terms of the prevention of hemolysis when the surface of the hollow fiber membrane filter medium has a reduced wettability because capillary effects during the first contact with blood can be reduced and the flux during the filtration process can also be reduced. A reduced wettability can e.g. be achieved by applying a coating, which has a reduced hydrophilicity. Without being bound to theory, it is assumed that a "low" wettability is highly advantageous for whole blood filtration. In this regard, "low" wettability means that a water or blood droplet should have a contact angle of about 60°-90°, preferably of about 80°-89.9°, on a reference planar surface made of borosilicate glass which was treated with the same chemical coating agents. In this case the wettability is reduced compared to an uncoated surface, but the coated surface is still hydrophilic according to the following definition: Hydrophilic surfaces lead to a water or blood droplet contact angle smaller than 90°, hydrophobic surfaces lead to a water or blood droplet contact angle bigger than 90°. Thus, the term "low" wettability preferably does not cover hydrophobicity of the surface. For the case of hydrophobic surface properties of a membrane, a higher transmembrane pressure would be necessary which would lead to slower and lower plasma recovery and/or to a damage of blood cells and therefore to hemolysis.

The wettability can be determined e.g. on coated glass slides: The contact angle of water on an uncoated and hydrophilic glass surface is about 44°, the contact angle of water on coated glass can be about 60°-90° depending on the coating process and the water droplet size.

Any medium or material which shows no interaction with whole blood is generally described as "hemocompatible". No interaction means especially that the medium or material does not cause blood clotting, e.g. by interacting with the blood coagulation system or the blood platelets. Accordingly, a hemocompatible material has no thrombotic effect. It is preferred that the hollow fiber membrane filter media according to the present invention are hemocompatible. Furthermore, it is preferred that the filter media do not modify any blood component concentrations by adsorption or reaction and that the contact with whole blood does not cause hemolysis.

It is advantageous for the hemocompatibility and for preventing the absorption of blood components when the surface of a material is negatively charged. This can be measured by determining the surface potential by a flow potential measurement. The interface between a solid surface and a surrounding liquid shows an electrical charge distribution, which is different from the solid and liquid bulk phases. In the model of the electrochemical double layer, this charge distribution is divided into a stationary and a mobile layer, which is separated by a shear plane. The zeta potential is assigned to the potential decay between the solid surface and the bulk liquid phase at this shear plane. The application of an external pressure gradient parallel to the solid/liquid interface leads to a relative motion between the stationary and mobile layers and to a charge separation which gives experimental access to the zeta potential. A dilute electrolyte is circulated through the measuring cell containing the solid sample, in case of the present invention the surface of the ceramic hollow fiber membrane filter medium. A relative movement of the charges in the electrochemical double layer occurs and gives rise to the streaming potential. This streaming potential—or alternatively the streaming current—is detected by electrodes placed at both sides of the sample. The zeta potential is calculated from the streaming potential or from the streaming current. The electrolyte conductivity, temperature and pH value are determined simultaneously. The measurements can be performed with the analysis device SurPASS of the company Anton Paar.

In a first embodiment, the present invention is directed to a whole blood hollow fiber membrane filter medium including a ceramic material having pore of a pore size ensuring permeability to blood plasma or serum, but retaining blood cells. Preferably, the whole blood hollow fiber membrane filter medium consists of a ceramic material having pores of a pore size ensuring permeability to blood plasma, but retaining blood cells.

In a preferred embodiment, the present invention is directed to a whole blood hollow fiber membrane filter medium including a ceramic material having pores of a pore size ensuring permeability to blood plasma.

In a preferred embodiment, the pore size of the whole blood hollow fiber membrane filter medium of the invention ensures permeability to all components of blood plasma/serum, in particular to electrolytes, lipid metabolism substances, markers, e.g. for infections or tumors, enzymes, substrates, proteins, and even pharmaceuticals and vitamins. Accordingly, it can be ensured that a subsequent analysis of the blood plasma/serum is based on an unchanged molecular composition of the respective components and, accordingly, an adequate determination of the required analytes is possible.

In a preferred embodiment, the whole blood hollow fiber membrane filter medium is a whole blood hollow fiber membrane cross-flow filter medium. It can either be used for out-in or for in-out cross-flow filtration. In-out cross-flow filtration is preferred due to the advantages of the cell distribution inside of the above mentioned flow conditions. Amounts of whole blood, which can be filtered with the whole blood hollow fiber membrane filter medium of the invention, are preferably in the range of from about 0.01 to about 10 ml, more preferably from about 0.1 ml to about 5 ml, most preferably from about 0.5 ml to about 3 ml. Preferably at least about 0.005 ml blood plasma/serum, more preferably at least about 0.05 ml, most preferably at least about 0.25 ml blood plasma/serum, can be obtained from the above amounts of whole blood.

In order to allow for cross-flow filtration, preferably in-out cross-flow filtration, the whole blood hollow fiber membrane filter medium of the invention is preferably open at both ends. At these ends, the whole blood hollow fiber membrane filter is preferably connected to pumping devices to impose the differential pressure which is required for the flux and for the filtration process. Preferably, the whole blood hollow fiber membrane filter medium is surrounded by a tubular housing, which has an opening for the filtrate release when used in an in-out cross-flow filtration process.

With the above mentioned pumping devices, several blood passages of the whole blood through the filter module can be performed. Preferably about 1 to about 80 blood passes are realized, more preferably about 10 to about 40 blood passes are realized. Within each blood pass, a certain amount of plasma/serum is removed from the whole blood passing the porous filter medium and the whole blood as the feed fluid is thickened due to the increasing blood cell concentration. The number of blood passes depends on the cell concentration of the whole blood sample, the age of the whole blood sample, the patient's state of health, the number of hollow fiber membranes within the filter module, the fiber properties, the filtration velocity, the system pressure, and the required volume of the separated plasma/serum. The over pressure inside of the filter module should be at most about 1.5 bar, preferably at most about 1.2 bar, most preferably about 1.0 bar, compared to the ambient pressure. The over pressure is imposed to overcome the transmembrane pressure drop and the pressure drop of the macroscopic flux through the hollow fiber bore channel.

In another preferred embodiment, the whole blood hollow fiber membrane filter medium is a whole blood hollow fiber membrane dead-end filter medium.

In another preferred embodiment, the whole blood hollow fiber membrane filter medium of the invention allows molecules of less than about 8,000 kDa, preferably less than about 10,000 kDa, more preferably less than about 20,000 kDa, to pass. In other words, the molecular weight cut-off (MWCO) is above 8,000 kDa, preferably above 10,000 kDa, more preferably above 20,000 kDa. As a consequence, erythrocytes, leukocytes, and thrombocytes are retained, but blood plasma components are not retained.

In another preferred embodiment, the median pore diameter of the whole blood hollow fiber membrane filter medium of the invention is at least about 100 nm, preferably at least about 150 nm, and more preferably at least about 190 nm. Preferably, the median pore diameter is in the range from about 100 nm to about 1,500 nm, more preferably from about 150 nm to about 1,300 nm, most preferably from about 190 nm to about 1,280 nm.

In terms of the prevention of hemolysis, it is preferred that that the median pore diameter is preferably in the range of from about 100 nm to about 400 nm, preferably from about 150 nm to about 300 nm, more preferably from about 190 nm to about 250 nm.

In terms of ensuring permeability to blood plasma or serum, it is preferred that the median pore diameter is preferably in the range of from about 200 nm to about 1,500 nm, preferably in the range of from about 300 nm to about 1,500 nm, more preferably in the range of from about 600 nm to about 1,400 nm, and most preferably in the range of from about 1,100 nm to about 1,400 nm.

An advantageous range for the median pore diameter in terms of both properties may therefore be from about 200 nm to about 1,300 nm, preferably from about 300 nm to about 600 nm.

In another preferred embodiment, the D10 pore diameter is in the range from about 150 to about 5,000 nm, preferably from about 200 to about 4,500 nm.

In another preferred embodiment, the D90 pore diameter is in the range from about 30 to 1,000 nm, preferably from about 50 to about 750 nm.

It is particularly preferred that the D10/D90 ratio is not more than 15, preferably not more than 12, more preferably not more than 10.

In terms of the prevention of hemolysis, it is preferred that the D10 pore diameter is in the range of from about 150 nm to about 500 nm, preferably from about 200 nm to about 400 nm, and that the D90 pore diameter is the range of from about 50 nm to about 200 nm, preferably from about 50 nm to about 150 nm.

In terms of ensuring permeability to blood plasma or serum, it is preferred that the D10 pore diameter is in the range of from about 200 nm to about 5,000 nm, preferably from about 1,000 nm to about 4,500 nm, more preferably from about 2,000 nm to about 4,200 nm, and that the D90 pore diameter is in the range of from about 150 nm to about 1,000 nm, preferably from about 200 nm to about 800 nm, most preferably from about 200 nm to about 700 nm.

An advantageous range for the D10 pore diameter in terms of both properties may therefore be from about 200 nm to about 5,000 nm, preferably from about 300 nm to about 4,000 nm, more preferably from 500 nm to 2,500 nm, and an advantageous range for the D90 pore diameter may be from about 100 nm to about 800 nm, preferably from about 150 nm to about 700 nm, more preferably from about 200 nm to about 400 nm.

In another preferred embodiment, the average pore diameter of the whole blood hollow fiber membrane filter medium of the invention is in the range from about 100 nm to about 1,500 nm, preferably from about 150 nm to about 1,300 nm, more preferably from about 150 nm to about 1,250 nm.

In terms of the prevention of hemolysis, it is preferred that the average pore diameter is in the range of from about 100 nm to about 500 nm, preferably from about 100 nm to about 300 nm, more preferably from about 100 nm to about 200 nm.

In terms of ensuring permeability to blood plasma or serum, it is preferred that the average pore diameter is in the range of from about 200 nm to about 1,500 nm, preferably from about 350 to about 1,300 nm, more preferably from about 400 nm to about 1,300 nm, most preferably from about 600 nm to about 1,250, particularly preferably from about 1,000 nm to about 1,250 nm.

An advantageous range for the average pore diameter in terms of both properties may therefore be from about 150 nm to about 1,000 nm, preferably from about 200 nm to about 600 nm.

In a preferred embodiment, the median pore diameter is in the range from about 100 nm to about 1,500 nm, more preferably from about 150 nm to about 1,300 nm, most preferably from about 190 nm to about 1,280 nm, and the average pore diameter is in the range from about 100 nm to about 1,500 nm, preferably from about 150 nm to about 1300 nm, more preferably from about 150 nm to about 1,250 nm.

In terms of the prevention of hemolysis, it is preferred that that the median pore diameter is preferably in the range of from about 100 nm to about 400 nm, preferably from about 150 nm to about 300 nm, more preferably from about 190 nm to about 250 nm, and that the average pore diameter is in the range of from about 100 nm to about 500 nm, preferably from about 100 nm to about 300 nm, more preferably from about 100 nm to about 200 nm.

In terms of ensuring permeability to blood plasma or serum, it is preferred that the median pore diameter is preferably in the range of from about 200 nm to about 1,500 nm, preferably in the range of from about 300 nm to about 1,500 nm, more preferably in the range of from about 600 nm to about 1,400 nm, and most preferably in the range of from about 1,100 nm to about 1,400 nm, and that the average pore diameter is in the range of from about 200 nm to about 1,500 nm, preferably from about 350 to about 1,300 nm, more preferably from about 400 nm to about 1,300 nm, most preferably from about 600 nm to about 1,250, particularly preferably from about 1,000 nm to about 1,250 nm.

An advantageous range for the median pore diameter in terms of both properties may therefore be from about 200 nm to about 1300 nm, preferably from about 300 nm to about 600 nm, and an advantageous range for the average pore diameter in terms of both properties may therefore be from about 150 nm to about 1000 nm, preferably from about 200 nm to about 600 nm.

In a preferred embodiment, the whole blood hollow fiber membrane filter medium according to the present invention comprises a ceramic material, wherein the ceramic material comprises a non-oxide material, which is preferably selected from the group consisting of a silicon carbide.

In another preferred embodiment, the whole blood hollow fiber membrane filter medium according to the present invention comprises a ceramic material, wherein the ceramic material comprises an alumosilicate or magnesium silicate, preferably a zeolite, and/or a calcium titanate, preferably a perovskite.

In another preferred embodiment, the ceramic material of the whole blood hollow fiber membrane filter medium comprises a metal oxide. Preferably, the ceramic material comprises a metal oxide selected from the group consisting of aluminum oxide, silicon oxide, titanium oxide, zirconium oxide, yttrium oxide and any combinations thereof. More preferably, the ceramic material comprises aluminum oxide in an amount of at least about 98 wt.-%, most preferably in an amount of at least about 99 wt.-%, based on the total weight of the ceramic material. It is also preferred that the ceramic material comprises aluminum oxide in an amount of at least about 98 wt.-%, preferably in an amount of at least about 99 wt.-%, more preferably in an amount of from about 99.5 to about 99.9 wt.-%, based on the total weight of the ceramic material, and further comprises at least one further metal oxide, e. g. titanium dioxide, in an amount of from about 0 wt.-% to about 2 wt.-%, preferably from about 0.1 wt.-% to about 1 wt.-%, more preferably from about 0.1 wt.-% to about 0.5 wt.-% based on the total weight of the ceramic material. It is particularly preferred that the modification of the aluminum oxide is alpha aluminum oxide ($\alpha$-$Al_2O_3$). Alpha aluminum oxide is typically formed by sintering the ceramic material at temperatures higher than 1,100° C. Thus, it is particularly preferred that the ceramic material comprises sintered alpha aluminum oxide, preferably in an amount of at least 98 wt.-%, more preferably in an amount of at least 99 wt.-%, most preferably in an amount of at least 99.5 wt.-%, based on the total weight of the ceramic material. Preferably, the ceramic material of the whole blood hollow fiber membrane filter medium of the invention comprises sintered alpha aluminum oxide in an amount of about 99.5 wt.-% to about 99.9 wt.-% based on the total weight of the ceramic material and a further metal oxide, wherein the at least one further metal oxide is preferably present in an amount of from about 0.1 wt.-% to about 0.5 wt.-% based on the total weight of the ceramic material. It has to be understood that the above wt.-% values refer to the total weight of the ceramic material after it has been sintered.

In another preferred embodiment, the volumetric median particle diameter of the aluminum oxide, of which the ceramic material is made, is from about 0.1 µm to about 2.0 µm, preferably from about 0.1 µm to about 1.5 µm. Aluminum oxide powders and other ceramic powders with a particle size in this range are commercially available, e.g. from Sasol or Almatis. The above particle size range is not only preferred for the aluminum oxide employed as starting material in the formation of the ceramic material, but can typically still be detected in the final ceramic material.

In another preferred embodiment, the whole blood hollow fiber membrane filter medium has an outer diameter of from about 0.4 mm to about 3.0 mm, preferably from about 0.4 mm to about 2.5 mm, more preferably from about 0.5 mm to about 2.0 mm.

In yet another preferred embodiment, the whole blood hollow fiber membrane filter medium has an inner diameter of from about 0.2 mm to about 2.0 mm, preferably from about 0.3 mm to about 1.5 mm, more preferably from about 0.3 mm to about 1.3 mm, provided that the inner diameter is lower than the outer diameter.

It is particularly preferred that the whole blood hollow fiber membrane filter medium has an outer diameter of from about 0.5 mm to about 2.0 mm and an inner diameter of from about 0.3 mm to about 1.3 mm.

In a preferred embodiment, the ratio of the outer diameter $D_o$ of the whole blood hollow fiber membrane filter medium to the inner diameter $D_i$ of the whole blood hollow fiber membrane filter medium, i.e. $D_o/D_i$, is in the range of from about 1.3 to about 2.0, preferably from about 1.4 to about 2.0, more preferably from about 1.6 to about 1.8.

In yet another preferred embodiment, the whole blood hollow fiber membrane filter medium has a wall thickness of about 0.1 mm to about 1.0 mm, preferably about 0.1 mm to about 0.8 mm, more preferably from about 0.1 mm to about 0.5 mm.

In yet another preferred embodiment, the whole blood hollow fiber membrane filter medium has a length of about 0.5 cm to about 8 cm. Preferably, a single whole blood hollow fiber membrane filter medium of this length has a filter area of from about 3 $mm^2$ to about 500 $mm^2$, preferably from about 10 $mm^2$ to about 450 $mm^2$, more preferably from about 100 $mm^2$ to about 300 $mm^2$ concerning one single hollow fiber membrane.

The filter area is the cross section area, which is covered by the feed flow in a filtration process. In the case of hollow fiber membrane filter media in an out-in filtration mode, it is the macroscopic cylindrical outer surface of all hollow fiber membranes in a filter module, which is wetted by the feed flow, i.e. the whole blood for the purpose of the present invention. In the case of hollow fiber membrane filter media in an in-out filtration mode, it is the macroscopic cylindrical inner surface of all hollow fiber membranes in a filter module, which is wetted by the feed flow, i.e. the whole blood for the purpose of the present invention.

If the hollow fiber membrane filter medium is porous, the filter area is different from the total material "inner" surface as the total material surface comprises the surfaces of all pores within the volume of the filter medium.

Accordingly, the structure of the whole blood hollow fiber membrane filter medium is additionally characterized by a porosity, which is preferably from about 30% to about 70%, more preferably from about 40% to about 65%, most preferably from about 43% to about 60%. This can be measured with the previously mentioned mercury intrusion porosimetry.

It has to be understood that the above listed preferred embodiments of the whole blood hollow fiber membrane filter medium regarding the pore size and structure as well as the parameters related to the size and shape of the fiber may apply to whole blood hollow fiber membrane filter medium in combination. For example, the following combinations a, b, c and d of preferred embodiments may be applicable for a whole blood hollow fiber membrane filter medium, which may e.g. be used as a cross-flow filter module as described above. The combinations are advantageous in terms of preventing hemolysis and ensuring permeability of blood plasma or serum, wherein the focus may slightly differ.

|   | D10 pore diameter [nm] | Median pore diameter (D50) [nm] | D90 pore diameter [nm] | Average pore diameter [nm] | Inner diameter [mm] | Outer diameter [mm] | Wall thickness [mm] | Accessible Porosity [%] |
|---|---|---|---|---|---|---|---|---|
| A | 150-5000 | 100-1500 | 30-1000 | 100-1500 | 0.2-2.0 | 0.4-3.0 | 0.1-1.0 | 30-70 |
| B | 200-400 | 190-250 | 50-150 | 100-200 | 0.3-1.5 | 0.4-2.5 | 0.1-0.8 | 40-65 |

-continued

|   | D10 pore diameter [nm] | Median pore diameter (D50) [nm] | D90 pore diameter [nm] | Average pore diameter [nm] | Inner diameter [mm] | Outer diameter [mm] | Wall thickness [mm] | Accessible Porosity [%] |
|---|---|---|---|---|---|---|---|---|
| C | 2000-4200 | 1100-1400 | 200-700 | 1000-1250 | 0.3-1.5 | 0.4-2.5 | 0.1-0.8 | 40-65 |
| D | 500-2500 | 300-600 | 200-400 | 200-600 | 0.3-1.5 | 0.4-2.5 | 0.1-0.8 | 40-65 |

In case of the above combinations of embodiments a, b, c and d, the ceramic material comprises aluminum oxide, and optionally at least one further metal oxide, as outlined in detail above.

In a further embodiment, the present invention is directed to a whole blood hollow fiber membrane filter medium including a ceramic material having a pore size ensuring permeability to blood plasma, but retaining blood cells, wherein the whole blood hollow fiber membrane filter medium is modified. A modification can be a coating of the hollow fiber membrane material, a pre-treatment or a pre-wetting e.g. a pre-wetting with a subsequent drying, or even a pre-wetting with a subsequent usage of the membrane material in a wetted state.

For obtaining such a modified whole blood hollow fiber membrane filter medium, any one of the above described whole blood hollow fiber membrane filter media can be taken and subjected to a modification. By coating or pre-wetting, hemolysis can effectively be prevented even at higher values for the median pore diameter, the D10 pore diameter, the D90 pore diameter, and the average pore diameter. Accordingly, it can be ensured at the same time that hemolysis is prevented and that the blood plasma or serum components to be analyzed are not retained in substantial amounts.

Therefore, in one embodiment it is preferred that a whole blood hollow fiber membrane filter medium is pre-wetted and has
(i) a median pore diameter in the range of from about 200 nm to about 1,500 nm, preferably from about 200 nm to about 1,000 nm, more preferably from about 200 nm to about 600 nm, most preferably in the range of from about 200 nm to about 400 nm;
(ii) a D10 pore diameter in the range of from about 200 nm to about 5,000 nm, preferably from about 200 nm to about 2,000 nm, more preferably from about 200 nm to about 800 nm;
(iii) a D90 pore diameter in the range of from about 150 nm to about 1,000 nm, preferably from about 150 nm to about 600 nm, more preferably from about 150 nm to about 400 nm; and
(iv) an average pore diameter in the range of from about 200 nm to about 1,500 nm, preferably from about 200 nm to about 1,000 nm, more preferably from about 200 nm to about 800 nm, most preferably in the range of from about 200 nm to about 600 nm, and particularly preferably from about 200 nm to about 400 nm.

In another embodiment, it is preferred that a whole blood hollow fiber membrane filter medium is coated and has
(i) a median pore diameter in the range of from about 200 nm to about 1,500 nm, preferably from about 300 nm to about 1,500 nm, more preferably from about 600 nm to about 1400 nm, most preferably in the range of from about 1,100 nm to about 1,400 nm;
(ii) a D10 pore diameter in the range of from about 200 nm to about 5,000 nm, preferably from about 1,000 nm to about 4,500 nm, more preferably from about 2,000 nm to about 4,200 nm;
(iii) a D90 pore diameter in the range of from about 150 nm to about 1,000 nm, preferably from about 200 nm to about 800 nm, more preferably from about 200 nm to about 700 nm; and
(iv) an average pore diameter in the range of from about 200 nm to about 1,500 nm, preferably from about 350 nm to about 1,300 nm, more preferably from about 400 nm to about 1,300 nm, most preferably in the range of from about 600 nm to about 1,250 nm, and particularly preferably from about 1,000 nm to about 1,250 nm.

More preferably, a whole blood hollow fiber membrane filter medium is coated and has
(i) a median pore diameter in the range of from about 200 nm to about 1,500 nm, preferably from about 300 nm to about 1,500 nm, more preferably from about 600 nm to about 1,400 nm, most preferably in the range of from about 1,100 nm to about 1,400 nm;
and
(iv) an average pore diameter in the range of from about 200 nm to about 1,500 nm, preferably from about 350 nm to about 1,300 nm, more preferably from about 400 nm to about 1,300 nm, most preferably in the range of from about 600 nm to about 1,250 nm, and particularly preferably from about 1,000 nm to about 1,250 nm.

Even more preferably, a whole blood hollow fiber membrane filter medium is coated and has
(i) a median pore diameter in the range of from about 1,100 nm to about 1,400 nm;
and
(iv) an average pore diameter in the range of from about 1,000 nm to about 1,250 nm.

In particular, a whole blood hollow fiber membrane filter medium according to combination c of preferred embodiments may be coated or pre-wetted, preferably coated, to obtain a modified whole blood hollow fiber membrane filter medium, in order to obtain a whole blood hollow fiber membrane filter medium which effectively ensures permeability to blood plasma or serum and, at the same time, prevents hemolysis. However, since coating or pre-wetting is in any case advantageous for preventing hemolysis, it also has to be understood that whole blood hollow fiber membrane filter media according to other combinations of preferred embodiments, such as combinations a, b, and d, may be modified according to the present invention.

In a preferred embodiment, the whole blood hollow fiber membrane filter medium is pre-wetted with salt solution, or a blood stabilization agent such as a heparin solution, or a combination of the foregoing. If the whole blood hollow fiber membrane filter medium has a length of from about 0.5 cm to about 8 cm, it is most preferable to use from about 0.1 ml to about 3 ml of the corresponding solutions for pre-wetting. Pre-wetting is advantageous because the pores are filled with liquid. Otherwise the hydrophilic surface property of the ceramic material (in combination with the porosity and the pore size distribution) would lead to high capillary forces during "soaking up" the plasma/serum and to a rupture of blood cells. No capillary forces occur after contact with the whole blood sample when the pores are already filled with an adequate fluid.

When pre-wetting the whole blood hollow fiber membrane filter medium, it is important to choose a suitable solution, which has the same ion strength as plasma/serum, to avoid hemolysis due to osmotic changes. A dilution of the plasma concentration, due to the additional fluid in the pores, and a change in the electrolyte concentration, e.g. sodium and chloride in the case of a sodium chloride solution, have to be taken into account for the subsequent plasma analysis.

Preferably, the whole blood hollow fiber membrane filter medium is pre-wetted with a sodium chloride solution, preferably an isotonic sodium chloride solution, more preferably a 0.9% sodium chloride solution (w:v, i.e. 9 g/L), and preferably not dried. It is most preferable that the whole blood hollow fiber membrane filter medium is directly used after pre-treatment, in order to avoid crystallization of sodium chloride at the surface which is called membrane scaling. Without being bound to theory, it is presently believed by the inventors that the formation of sodium chloride crystals should preferably be avoided because the sharp edges of these crystals can damage erythrocytes, thereby causing hemolysis. In a preferred embodiment, pre-wetting means dipping of the whole blood hollow fiber membrane filter medium into an adequate liquid, flushing the whole blood hollow fiber membrane filter medium with an adequate liquid or contacting the whole blood hollow fiber membrane filter medium with the liquid surface of an adequate liquid.

The whole blood hollow fiber membrane filter medium may also be pre-wetted with a heparin solution. For example, a heparin solution suitable for treatment of thrombosis, such as Fraxiparine including nadroparin calcium or heparin-sodium-25000 (ratiopharm), may be used. Preferably, one syringe with 0.8 ml heparin solution comprises nadroparin calcium 7.600 International Unit I.U, anta-Xa (corresponding to 95 I.U. to 130 I.U. anti-Xa/mg). Further components may be calcium hydroxide/hydrochloride acid 10% for pH adjustment and water.

Still further, the whole blood hollow fiber membrane filter medium may be pre-wetted with a citrate buffer solution.

Still further, the whole blood hollow fiber membrane filter medium may be pre-wetted with an EDTA (ethylenediaminetetraacetic acid) buffer solution.

In another preferred embodiment, the whole blood hollow fiber membrane filter medium is coated. Preferably, the coating is suitable for reducing the hydrophilicity and wettability of the filter medium surface. By such a coating, the capillary forces, which induce hemolysis at the first contact of the porous membrane filter material with whole blood, can be reduced. Furthermore, a reduced hydrophilicity and wettability results in a reduced flux through the hollow fiber membrane filter medium during the filtration process on the other side.

In order to obtain a reduced hydrophilicity and a low wettability of the surface, the coatings have to increase the contact angle between aqueous droplets and the solid plane surface. Further requirements on the coating are as follows:
No plugging of pores, and therefore no film-building structure
Building up a homogeneous and stable coating layer
Hemocompatibility: No generation of hemolysis due to the chemistry and no adherence and/or cross-reactions with the plasma/serum analytes.

This can be achieved with e.g. fluorine-containing coating materials (e.g. products from the series "Dynasylan" from Evonik Industries or products from the series "Nuva" from Clariant), such as bifunctional silanes with hydrolyzable inorganic ethoxysilyl and fluoroalkyl chains (e.g. available under the trade name DYNASYLAN® F 8261 from Evonik Industries) or fluoroalkyl-functional oligosiloxanes (e.g. available under the trade name DYNASYLAN® F 8815 from Evonik Industries) for dip coating. Coating out of the gas phase is also possible with a plasma enhanced coating technology or with a sol-gel technology. Fluorine-containing molecules have the advantage that they not only establish a reduced hydrophilicity of the surface, but also an oleophobic property. This reduces the risk of adherence for non-polar substances like proteins and lipids. The extent of the reduction of hydrophilicity and the increase of oleophobicity is not only dependent on the coating substance but also on its concentration in the coating liquid (or gas), when the coating is applied, as well as on the coating process parameters, like coating procedure, temperature, and contact time.

Different methods can be performed to apply the coating to a surface. A procedure for coating a porous ceramic material with e.g. fluorosilanes to obtain a reduced hydrophilicity of the surface is e.g. described in DE 19937325 B4.

In in-out cross-flow filtration, the coating is especially necessary at the inner filter area of the whole blood hollow fiber membrane filter medium, where the blood contacts the membrane material first. Preferably, the coating may be applied by using a dip coating procedure with a coating liquid, wherein the fluorine coating product is e.g. dissolved in an additional solvent. It is possible to dilute the coating product with an additional solvent to adjust the extent of the reduction of the hydrophilicity. As additional solvent, ethanol or water may be used.

The coating liquid with the diluted coating substances can be applied
By dip coating
In a dead-end mode: One end of the whole blood hollow fiber membrane filter medium is sealed and the coating fluid has to pass through the pores after pressure is induced.
In an open-end mode: The coating fluid passes through the inner side of the whole blood hollow fiber membrane filter medium without the influence of pressure and therefore wets only the surface.

Additionally, a post-treatment of the coating can be performed to ensure that excess coating fluid is removed. This can be done by directly flushing the whole blood hollow fiber membrane filter media after the coating process. The selection of the flushing fluid depends on the coating material itself. Some coatings have an aqueous basis, some have solvent as basis. Apart from dipping, flushing can be performed also either dead-end or open-end. From this follow four different coating combinations for every coating solution.

For example, the inner filter area of a hollow fiber membrane filter medium of a length of about 19 cm may be coated with about 2 ml of coating liquid. This coating liquid is preferably charged only on the inner surface of the hollow fiber filter medium by introducing a cannula into one hollow fiber opening. This charging can be done with an open-end hollow fiber where the coating liquid drains off the second opening of the hollow fiber membrane filter, or with a closed-end hollow fiber where pressure has to be induced to pump the coating liquid through the pores. To remove the supernatant coating liquid, a subsequent flushing with 2 ml of solvent is performed. Also in this case the hollow fiber can be either in an open-end or in a closed-end state.

In another preferred embodiment, the whole blood hollow fiber membrane filter medium is modified, e.g. by negatively charging its surface to improve hemocompatibility and to reduce protein adsorption on the solid surface. Preferably, the inner filter area of the whole blood hollow fiber membrane filter medium is negatively charged when the filter medium is used in an in-out cross-flow filtration.

In yet another preferred embodiment, the whole blood hollow fiber membrane filter medium is coated in that the surface, preferably the inner filter area, of the whole blood hollow fiber membrane filter medium carries at least one type of functional groups selected from the group consisting of carboxylate groups, amino groups, silane groups, and any combinations thereof to improve hemocompatibility.

In a further embodiment, the present invention is directed to a whole blood hollow fiber membrane filter medium as described above, which is obtainable by a phase inversion process. In this regard, the whole blood hollow fiber membrane filter medium is preferably obtainable from a viscous spinning dope including at least a ceramic powder material, a polymer and a solvent, wherein the ceramic powder material preferably comprises aluminum oxide, the polymer is preferably polyacrylonitrile or polyethersulfone and the solvent is preferably n-methyl-pyrrolidone. It is particularly preferred that the volumetric median particle diameter of the aluminum oxide is from about 0.1 µm to about 2.0 µm, preferably from about 0.1 µm to about 1.5 µm. Preferably, the spinning dope is conducted through the annulus cross-section of a multiple-component nozzle to give the green fiber. In terms of the pore size and pore shape of the whole blood hollow fiber membrane filter medium, it is particularly preferred that the green fiber is sintered at a temperature from about 1,350° C. to about 1,700° C. for a time interval of from 1.5 to 12 hours.

In another aspect, the present invention is directed to the use of a whole blood hollow fiber membrane filter medium as defined above, i.e. either not modified or modified, i.e. not pre-treated or pre-treated, not pre-wetted or pre-wetted, or uncoated or coated, for separating blood plasma/serum from a whole blood sample. Preferably, the blood plasma/serum, which is obtained, shows no or substantially no hemolysis.

In a preferred embodiment, the blood plasma/serum is separated from the whole blood sample by cross-flow-filtration by using any one of the whole blood hollow fiber membrane filter media according to the present invention described above.

Preferably, cross-flow filtration is performed by passing the whole blood along the longitudinal extension of the whole blood hollow fiber membrane filter medium, optionally alternately in both directions, by applying positive pressure in respect of ambient pressure, preferably positive pressure from about 0.5 bar to about 1.5 bar. Most preferably, the positive pressure is about 0.5 bar.

Alternatively, cross-flow filtration is performed by passing the whole blood along the longitudinal extension of the whole blood hollow fiber membrane filter medium, optionally alternately in both directions, by applying negative pressure in respect of ambient pressure, preferably negative pressure from about 0.5 bar to about 1.0 bar. Most preferably, the negative pressure is about 0.5 bar.

According to the present invention, cross-flow filtration may be performed as in-out cross-flow filtration or out-in cross-flow filtration, preferably as in-out cross-flow filtration.

The present invention is directed to the use of any one of the whole blood hollow fiber membrane filter media as defined above, i.e. either not modified or modified, for separating blood plasma/serum from a whole blood sample, wherein the whole blood sample is diluted with isotonic sodium chloride solution. Preferably, the whole blood sample is diluted with isotonic sodium chloride solution, in a ratio of from 0.5:1 to 1:5, preferably in a ratio of from 1:1 to 1:4.

Furthermore, the present invention is directed to the use of any one of the whole blood hollow fiber membrane filter media as defined above, i.e. either not modified or modified, for separating blood plasma from a whole blood sample, wherein the whole blood sample is stabilized with an anti-coagulation agent selected from the group consisting of EDTA, citrate, heparin, and combinations thereof.

Moreover, the present invention is directed to the use of any one of the whole blood hollow fiber membrane filter media as defined above, i.e. either not modified or modified, for separating blood plasma/serum from a whole blood sample, wherein the whole blood is pre-treated with a cell agglomeration agent, such as lectin.

It should be emphasized that the use of the whole blood hollow fiber membrane filter medium as defined above is particularly advantageous for separation processes such as the separation of blood plasma/serum from a whole blood sample when it is used by manually operating it because, in contrast to the use of a centrifuge, the use of the whole blood hollow fiber membrane filter medium is then possible without electricity. Furthermore, the use of the whole blood hollow fiber membrane filter medium is advantageous over the use of a centrifuge because it is less time consuming.

The whole blood hollow fiber membrane filter media according to the present invention may also be used as a solid-liquid or liquid-liquid separation tool in other fields, e.g. in veterinary medicine, food technology, environmental sciences, and in scientific laboratories in general. In particular, the whole blood hollow fiber membrane filter media can be used in efficient and mild separation methods of highly concentrated suspensions, cellular systems, and sensitive particulate systems. It is highly preferred to use the whole blood hollow fiber membrane filter media according to the present invention in filtration processes, wherein the volume of the sample to be separated and the volume of the filtrate is small, e.g. less than 20 ml, preferably less than 10 ml, which is e.g. the case in the analytical quality assurance in production processes.

The present invention is illustrated in further detail with reference to the following examples. However, the scope of the present invention is not limited to these examples.

EXAMPLES

Whole blood hollow fiber membrane filter media including aluminum oxide and having a length of about 4 cm-8 cm, D50 (volume related) median pore diameters in the range of from 150 to 1,300 nm, different outer and inner diameters as well as different wall thicknesses, different surface treatment state, and different numbers of fibers within one filtration module have been tested in the following examples.

Within these examples and tests, whole blood samples stabilized with heparin in an amount of about 1 ml to about 3 ml were filtered by means of in-out cross-flow filtration using a whole blood hollow fiber membrane filter medium as described above, in order to separate blood plasma from these whole blood samples.

For the filtration purpose, one or a plurality of whole blood hollow fiber membranes were fixed inside of a housing tube and connected to a syringe, at each end via teflon and silicone tubings, and arranged within and along the length of a tube with openings for removing the filtrate and for pressure compensation. After one of the two syringes was filled with the whole blood sample, 7 to 80 pump cycles from one syringe to the other were performed by applying an overpressure of about 0.5 bar to about 1.5 bar with the syringes, in order to cause the whole blood to pass along the longitudinal extension of the whole blood hollow fiber membrane filter medium, i.e. to tangentially pass across the inner filter area of the whole blood hollow fiber membrane filter medium. An amount 0.1 ml to 0.7 ml of blood plasma could be obtained within a time period of about 1-5 minutes as the filtrate in the tube. After the whole blood filtration, the filtrate was visually evaluated in terms of the degree of hemolysis. Furthermore, the retentate was visually evaluated in terms of hemolysis as well.

Additionally contact tests between the ceramic whole blood hollow fiber membrane material and heparin stabilized whole blood were conducted to analyze the generation of hemolysis due to material contact effects and without the influence of the dynamic forces occurring during the filtration process.

For testing the molecular retention of plasma analytes by the ceramic whole blood hollow fiber membrane, pre-centrifuged and heparin stabilized plasma was used as feed in an amount of about 1.5 ml to about 3 ml and filtered by the hollow fiber membrane filter media. Occasionally plasma samples were used which had been stored in the refrigerator for one week. For the plasma analysis, no filter module was applied as mentioned before to avoid plasma contact with too many different materials: Here, the in-out cross-flow filtration was performed with two parafilm-fixed standard medical cannulas within the hollow fiber membrane filter media to which the syringes are connected. The plasma filtrate is directly collected with a third syringe. The plasma analysis results from the filtered plasma and from the plasma retentate were compared to the plasma analysis results from a "reference sample" of the same plasma sample which had no contact to the filter module material, considering 15 different plasma components according to Table 8 and Table 12.

Furthermore, contact tests were conducted between the ceramic whole blood hollow fiber membrane material and pre-centrifuged and heparin stabilized plasma to measure possible adsorption of plasma analytes. The plasma analysis results were compared to the analysis results of a "reference sample" of the same whole blood sample which had no contact to the filter module material considering 15 different plasma components according to Table 6 and Table 12.

In Table 1, the different ceramic hollow fiber membrane filter media are listed which were used for the test filtrations (the letters a, b, c, d, and e are related to different fibers). Fiber denominations with the same letter in the following Examples refer to the same fiber. The most important difference is the pore size.

TABLE 1

| Fiber | Pore diameter d10 [nm] | Median pore diameter d50 [nm] | Pore diameter d90 [nm] | Average pore diameter (hydraulic diameter) [nm] | Inner fiber diameter [mm] | Outer fiber diameter [mm] | Wall thickness [mm] | Zeta potential on the outer surface (at pH 7.4) [mV] | Arithmetical mean height of surface Sa (inner surface) [µm] | Accessible porosity [%] |
|---|---|---|---|---|---|---|---|---|---|---|
| a | 252 | 228 | 195 | 224 | 1.1 | 2.1 | 0.5 | — | 0.17 | 43.47 |
| b | 360 | 231 | 74 | 162 | 0.3 | 0.5 | 0.1 | — | — | 43.21 |
| C | 231 | 198 | 121 | 173 | 0.7 | 1.1 | 0.2 | — | — | 50.65 |
| D | 4105 | 1270 | 668 | 1199 | 1.1 | 2.0 | 0.45 | <−40 | 0.4 | 59.74 |
| E | 2242 | 389 | 239 | 431 | 1.1 | 2.0 | 0.45 | 7 | 0.13 | 55.72 |

Example 1

In Example 1, different ceramic hollow fiber membrane filter media were used for the filtration of whole blood. Whole blood samples were filtered by means of in-out cross-flow filtration. The different hollow fibers were mainly prepared as a single fiber module and the results are presented in the following Table 2.

TABLE 2

| Example | Length of fiber [mm] | Number of fibers [—] | Volume whole blood [ml] | Volume filtrate [ml] | Pump cycles [—] | Hemolysis* in filtrate | Hemolysis* in retentate |
|---|---|---|---|---|---|---|---|
| 1 a | 57 | 1 | 2 | 0.3 | — | m | m |
| 1 b | 49 | 5 | 2 | 0.3 | 7 | n | o |
| 1 c | 46 | 1 | 2 | 0.3 | — | n | n |
| 1 d | 46 | 1 | 1.8 | 0.4 | 30 | h | m |
| 1 e | 57 | 1 | 1.5 | 0.1 | 100 | h | h |

*o = no hemolysis, n = substantially no hemolysis, m = medium degree of hemolysis, h = high degree of hemolysis
— = no value tracked during experiment In Example 1 a, a medium degree of hemolysis was observed in both, the filtrate, i.e. the plasma, and the retentate. It is observed that the hemolysis decreased with increasing number of pump cycles and increasing plasma production indicating that hemolysis is an effect occurring only upon the first contact of the whole blood with the dry and hydrophilic membrane material.

In Example 1 b, substantially no hemolysis was observed in the filtrate, i.e. the plasma, and no hemolysis was observed in the retentate.

In Examples 1 b and 1 c, a lower degree of hemolysis was observed in both the filtrate, i.e. the plasma, and the retentate.

The observations in Example 1 e were similar to the results of 1 a: Hemolysis decreased with increasing number of pump cycles and increasing plasma production indicating that hemolysis is an effect occurring only upon the first contact of the whole blood with the dry and hydrophilic membrane material.

Example 2

It was also determined whether the whole blood hollow fiber membrane filter media including aluminum oxide and having D50 (volume related) pore sizes in the range of from 150 nm to 1,300 nm, in a dry or pre-wetted state induce hemolysis only by contact with a whole blood sample and without the influence of any filter module or further forces occurring during the filtration, e.g. caused by the flux.

Five pieces of 1 cm length each of different hollow fiber qualities were dipped into 2 ml of whole blood for 10 minutes. Then the pieces were removed from the blood samples which were centrifuged afterwards. After centrifugation, the supernatant plasma was optically evaluated in terms of hemolysis.

Pre-wetting was performed by rinsing the whole blood hollow fiber membrane filter medium with an aqueous pre-wetting solution in an amount of about 2 ml to 3 ml. As pre-wetting solution, a 0.9% sodium chloride solution (w:v) was applied. The pre-wetted whole blood hollow fiber membrane filter medium was directly used in a wetted state.

Results are shown in Table 3:

TABLE 3

| Example | Length of fiber | Hemolysis* in reference sample w/o fiber | Hemolysis* in sample with dry fiber | Hemolysis* in sample with pre-wetted** fiber |
|---|---|---|---|---|
| 2 d | 5 × 1 cm | o | m | ○ |
| 2 e | 5 × 1 cm | o | m | ○ |

*o = no hemolysis, n = substantially no hemolysis, m = medium degree of hemolysis, h = high degree of hemolysis, (—) = not determined
**NaCl = 0.9% sodium chloride solution (w:v)

As is apparent from Examples 2d and 2e, it has been found that a pre-wetting of the porous filter membrane with sodium chloride solution inhibits hemolysis.

Example 3

Modified and, in particular, pre-wetted whole blood hollow fiber membrane filter media including aluminum oxide and having a length of about 4 cm-8 cm and D50 (volume related) pore sizes in the range of from about 150 to about 1,300 nm, were used for whole blood filtration. Pre-wetted whole blood hollow fiber membrane filter media with different fiber lengths, different outer and inner diameters as well as different wall thicknesses have been tested.

Pre-wetting was performed by flushing the whole blood hollow fiber membrane filter medium with an aqueous pre-wetting solution in an amount of about 2 ml to 3 ml. The pre-wetting is conducted in the same manner as the blood filtration procedure, namely in an in-out cross-filtration process with two syringes, until the whole pre-wetting solution has passed the hollow fiber membrane filter material. With an aqueous pre-wetting solution, this process is quickly finished after 1-10 pumping cycles, depending on the manually generated transmembrane pressure. As pre-wetting solutions, a 0.9% sodium chloride solution (w:v) and a heparin solution including heparin-sodium were applied. The pre-wetted whole blood hollow fiber membrane filter medium was directly used in a wetted state.

Whole blood samples were filtered by means of in-out cross-flow filtration as described above, but by using a pre-wetted whole blood hollow fiber membrane filter medium with a single hollow fiber in order to separate blood plasma from these samples. The results in terms of hemolysis are presented in the following Table 4.

TABLE 4

| Example | Pre-wetting solution | Length of fiber [mm] | Volume whole blood [ml] | Volume filtrate [ml] | Pump cycles [—] | Hemolysis*** in filtrate | Hemolysis*** in retentate |
|---|---|---|---|---|---|---|---|
| 3 a-1 | NaCl* | 48 | 2 | 0.5 | 40 | N | n |
| 3 a-2 | Heparin** | 60 | 1 | 0.22 | 20 | O | m |
| 3 d-1 | NaCl* | 50 | 1.5 | 0.5 | 40 | M | m |
| 3 d-2 | Heparin** | 60 | 1 | 0.38 | 20 | h | m |
| 3 e-1 | NaCl* | 50 | 1.5 | 0.26 | 60 | o | m |
| 3 e-2 | Heparin** | 61 | 1 | 0.22 | 20 | o | m |

*NaCl = 0.9% sodium chloride solution (w:v)
**heparin solution including heparin-sodium 25000
***o = no hemolysis, n = substantially no hemolysis, m = medium degree of hemolysis, h = high degree of hemolysis, (—) = not determined It has been found that pre-wetting with sodium chloride solution and direct use of the whole blood hollow fiber membrane filter media of the invention is effective in preventing hemolysis in the filtrate (Examples 3 a −1). It is assumed that pre-wetting reduces the capillary forces.

Only in case of the whole blood hollow fiber membrane filter medium having a D50 pore size of about 1,270 nm, pre-wetting cannot efficiently prevent hemolysis (Examples 3 d −1). As already mentioned above, it is assumed that in this case the hemolysis is induced by the high flux through the big pores which causes cell rupture.

Wetting with a heparin solution and direct use of the whole blood hollow fiber membrane filter medium is also suitable for reducing hemolysis in the filtrate. Also other iso-osmotic fluids can be applied, e. g. phosphate buffered saline.

Example 4

For the experiments, whole blood hollow fiber membrane filter media including aluminum oxide and having a length of about 4 cm-8 cm and D50 (volume related) pore sizes in the range of from about 150 to about 1,300 nm, were used. No pre-treatment was performed with the ceramic whole blood hollow fiber membranes.

The whole blood sample to be separated was diluted with a 0.9% sodium chloride solution (w:v) prior to filtration in different ratios. The different dilution ratios are specified in the following Table 5.

The diluted whole blood samples were filtered by means of in-out cross-flow filtration as described in Example 1. The results in terms of hemolysis are presented in the following Table 5.

TABLE 5

| Example | Length of fiber [mm] | Ratio of NaCl* [%] | Volume whole blood [ml] | Volume filtrate [ml] | Pump cycles [—] | Hemolysis in the filtrate** | Hemolysis in the retentate** |
|---|---|---|---|---|---|---|---|
| 4 a-1 | 56 | 0 | 2 | 0.12 | 50 | m | o |
| 4 a-2 | 60 | 50 | 2 | 0.15 | 50 | m | o |
| 4 a-3 | 56 | 80 | 2 | 0.3 | 50 | n | o |

*NaCl = 0.9% sodium chloride solution (w:v)
**o = no hemolysis, n = substantially no hemolysis, m = medium degree of hemolysis, h = high degree of hemolysis,
(—) = not determined Both Examples 4 a −2 and 4 a −3 show that dilution of the whole blood sample is advantageous for reducing hemolysis because, especially in Example 4 a −3, the filtrate shows substantially no hemolysis. The dilution of the whole blood sample with sodium chloride solution reduces the viscosity of the samples and the relative amount of blood cells in the sample and therefore the blood cell concentration. As a consequence, mechanical influences causing hemolysis are reduced and capillary effects at the first contact are less destructive to the blood cells than with a pure whole blood sample with higher concentration of blood cells. Additionally, the filtrate amount increases with higher dilution of the whole blood sample.

Example 5

It was also determined whether certain plasma components are adsorbed by the whole blood hollow fiber filter media as used in Example 1, or a reaction of components from the filter media with plasma components occurs because this could falsify the amounts of plasma components determined in the plasma sample after cross-flow filtration.

The whole blood hollow fiber membrane filter media including aluminum oxide and having D50 (volume related) pore sizes in the range of from about 150 to about 1,300 nm, as used in Example 1 d and 1 e, were contacted with a plasma sample of 1 ml for 10 minutes using 5 pieces à 1 cm of each fiber. The amount of plasma components (analytes) in the applied plasma sample was then compared to the amount of plasma components (analytes) in the same sample called "reference", which was not contacted with a filter medium. The deviation was determined in percent and is shown for two measurements concerning both hollow fiber membrane qualities in Table 6. The two hollow fiber membrane qualities were used without modification in a dry state.

TABLE 6

| Plasma components | | Deviation of concentrations [%] | | | |
|---|---|---|---|---|---|
| | | 4 d −1 | 4 d −2 | 4 e −1 | 4 e −2 |
| Electrolytes | Potassium | 2.13 | 0.00 | 2.44 | 2.50 |
| | Sodium | 0.74 | −1.45 | 0.00 | −1.33 |
| | Calcium | −1.32 | 0.00 | −10.00 | −7.61 |
| | Magnesium | −2.38 | 0.00 | −8.14 | −6.45 |
| | Chloride | 0.00 | 0.00 | 0.00 | 0.00 |
| | Phosphate | −2.19 | −2.88 | −19.33 | −26.53 |
| Lipids | Triglyceride | 1.25 | −2.84 | 0.69 | −1.39 |
| | Cholesterol | 1.19 | −0.79 | −0.69 | 25.00 |
| | HDL cholesterol | 2.08 | −5.26 | 0.00 | 266.67 |
| | LDL cholesterol | 0.96 | 1.52 | −1.61 | −9.09 |
| Infection markers | CRP | −12.50 | −1.18 | −1.06 | −1.97 |

TABLE 6-continued

| Plasma components | | Deviation of concentrations [%] | | | |
|---|---|---|---|---|---|
| | | 4 d −1 | 4 d −2 | 4 e −1 | 4 e −2 |
| Enzymes | GOT/AST | 3.85 | 0.00 | 4.00 | 0.00 |
| | Lipase | −1.36 | 1.36 | 1.87 | 0.00 |
| Substrates | Albumin | 0.00 | 0.00 | 0.00 | 0.00 |
| | Bilirubin total | 0.00 | 0.00 | 0.00 | 5.00 |
| | Glucose | 1.08 | 1.59 | 0.00 | 0.00 |
| | Creatinine | 0.00 | 0.00 | 0.00 | −5.00 |
| Proteins | IgG | 1.99 | 1.34 | 4.73 | — |
| | Ferritin | 0.27 | 1.45 | 0.94 | — |

It was found that the Examples 4 d show lower deviations than the Examples 4 e. With the exception of the runaway values for phosphate for Examples 4 e −1 and −2 and the non-reproducible peaks for cholesterol for Examples 4 e −2, the deviations are low. The assumed explanation for the phosphate reduction is the different zeta potential on the surface of the different hollow fiber membrane filter media including aluminum oxide which leads to different adsorption behavior of molecular components on the membrane surface.

Example 6

It was also determined whether certain plasma components are removed upon cross-flow filtration as performed in Examples 1 and 3, e.g. due to a retention of molecular plasma analytes due to the small pore sizes of the whole blood hollow fiber membrane filter medium.

Whole blood hollow fiber membrane filter media as used in Examples 1 d and 1 e with filter module properties according to Table 7 were tested in this respect with an already centrifuged plasma sample and with a single hollow membrane fiber which was not modified.

Table 7 shows that due to the pore sizes the cell-free plasma can be quickly obtained by the hollow fiber membrane filter media "d" and needs more time to pass through the hollow fiber membrane filter media "e" because of the smaller pore sizes. The filtrate and retentate volumes were about 0.5 ml.

The amount of plasma components (analytes) in the filtrate and in the retentate samples obtained from an already centrifuged plasma by in-out cross-flow filtration as described above was compared to the amount of plasma components (analytes) obtained by the same whole blood "reference" sample without filtration. The analytes in the filtrate represent the molecules which pass through the membrane, the analytes in the retentate indicate if some molecules are retained by the membrane. The deviation was determined in percent referred to the "reference" sample and is shown in Table 8 for two measurements concerning both hollow fiber membrane qualities which were used without modification in a dry state.

TABLE 8

| | | Deviation of concentrations [%] | | | | | | | |
|---|---|---|---|---|---|---|---|---|---|
| | | 5 d-1 | | 5 d-2 | | 5 e-1 | | 5 e-2 | |
| | Plasma components | Filtrate | Retentate | Filtrate | Retentate | Filtrate | Retentate | Filtrate | Retentate |
| Electrolyte | Potassium | 0.00 | 2.70 | 5.26 | 0.00 | 12.12 | 0.00 | 12.77 | 0.00 |
| | Sodium | −0.68 | 1.36 | 1.40 | 0.00 | 0.00 | 0.00 | −0.69 | 0.00 |
| | Calcium | −0.44 | −17.54 | 0.44 | −1.32 | −45.45 | 1.24 | −47.81 | 0.44 |
| | Magnesium | −5.00 | — | −9.41 | −2.35 | −38.96 | 0.00 | −38.04 | 3.26 |
| | Chloride | 0.00 | 1.89 | 1.90 | −0.95 | 0.00 | 0.00 | 0.96 | 0.00 |
| | Phosphate | −1.67 | −10.00 | −4.26 | 1.06 | −73.76 | 1.42 | −94.39 | −1.87 |
| Lipids | Triglyceride | 7.37 | 3.16 | 1.52 | −1.52 | −29.73 | 2.70 | −28.57 | −1.90 |
| | Cholesterol | 1.60 | 4.79 | 1.22 | −0.61 | −47.73 | −0.76 | −41.20 | −1.72 |
| | HDL cholesterol | 0.00 | 2.50 | 1.79 | 1.79 | −4.17 | 2.08 | −4.00 | 2.00 |
| | LDL cholesterol | 0.00 | 6.36 | 1.05 | −2.11 | −88.71 | −4.84 | −54.32 | −3.09 |
| Infection markers | CRP | 1.26 | 5.23 | 0.00 | 11.11 | −94.33 | −2.76 | −86.79 | −13.21 |
| Enzymes | GOT/AST | 4.50 | 14.41 | 19.05 | 23.81 | 2.63 | 0.00 | −5.56 | 55.56 |
| | Lipase | 0.00 | 2.45 | 3.43 | −1.14 | −2.42 | −1.45 | 0.00 | −0.69 |
| Substrates | Albumin | 3.45 | 6.90 | 2.33 | 0.00 | 0.00 | −2.56 | 2.27 | 0.00 |
| | Bilirubin total | 0.00 | 0.00 | 33.33 | 33.33 | 0.00 | 0.00 | 0.00 | 0.00 |
| | Glucose | 1.32 | 3.29 | 2.04 | 1.36 | −1.26 | −0.63 | 0.87 | 0.87 |
| | Creatinine | 0.00 | 0.00 | 0.00 | −7.69 | 0.00 | 0.00 | 0.00 | 10.00 |
| Proteins | IgG | −6.24 | −3.33 | 1.98 | −7.91 | −2.75 | 3.05 | 18.22 | 3.72 |
| | Ferritin | 1.95 | 0.76 | 0.00 | −0.88 | −4.64 | 1.84 | −0.55 | −1.17 |

— = no value available

TABLE 7

| Example | Length of fiber [mm] | Volume of applied plasma [ml] | Pump cycles [—] |
|---|---|---|---|
| 5 d −1 | 84 | 1.8 | 1 |
| 5 d −2 | 84 | 1.8 | 0.5 |
| 5 e −1 | 65 | 2.2 | 10 |
| 5 e −2 | 65 | 1.7 | 10 |

The remaining amounts of plasma components are reduced for Example 5 e especially in the filtrate because the components are partly filtered off on the one side, and partly separated by adsorption due to the surface charge of the ceramic material (see Example 4). The effects are less pronounced in case of Example 5 d because the maximum pore size of the whole blood hollow fiber membrane filter medium is higher and, therefore, the permeability for plasma analytes is better; additionally, the surface charge of this material does not lead to the same degree of adsorption like seen in Example 5 e.

Example 7

It was also determined whether the filtration duration can be reduced by applying a plurality of whole blood hollow fiber filter media as used in Example 1 a in parallel. The results are shown in Table 9.

TABLE 9

| Example | Modification | Length of fiber [mm] | Number of fibers [—] | Whole blood [ml] | Plasma filtrate [ml] | Duration |
|---|---|---|---|---|---|---|
| 6 a-1 | NaCl*, wet fiber | 50 | 1 | 1.5 | 0.26 | 1:10 min.; 60 pump cycles |
| 6 a-2 | NaCl*, wet fiber | 33 | 8 | 2.0 | 0.6 | 0:40 min.; 40 pump cycles |

*NaCl = 0.9% sodium chloride solution (w:v)

It has been found that no hemolysis occurred for Examples 6 a as the hollow fiber filter media was used in a pre-wetted state. The application of eight fibers (Example 6 a –2) instead of only one fiber (Example 6 a –1) accelerated the filtration process: In a shorter time more filtrate was obtained (which was slightly diluted due to the pre-wetting).

Example 8

It has been tested whether a coating could be advantageous for the hollow fiber membrane filter medium quality "d". It is believed that a reduced hydrophilicity by a coating of the hollow fiber membrane filter medium or at least of the inner filter area of the hollow fiber membrane filter medium leads to a reduced wettability and therefore to reduced capillary effects during the first contact with blood on the one side and to a reduced flux through the hollow fiber membrane filter medium during the filtration process on the other side.

For this example, a fluorine containing product dissolved in ethanol is selected (Dynasylan F8261 from Evonik) to coat a ceramic whole blood hollow fiber membrane filter medium of the quality "d". For this example, a dilution of the coating product of 1:60 with ethanol is prepared to a coating liquid based on the manufacturer's information.

It is assumed that a "low" wettability is adequate for the whole blood filtration.

In this Example, a hollow fiber of about 19 cm length is coated with about 2 ml of coating liquid. This coating liquid is charged only on the inner filter area of the hollow fiber filter medium by introducing a cannula into one hollow fiber opening. To remove the supernatant coating liquid, a subsequent flushing with 2 ml of solvent is performed.

In Example 8 d –1, a coated ceramic hollow fiber membrane filter medium was used for the filtration of whole blood. Whole blood samples were filtered by means of in-out cross-flow filtration. The result of the filtration of blood with a coated hollow fiber membrane filter medium with reduced hydrophilicity is shown in Table 10.

It was also determined, whether certain plasma components are adsorbed by the coated whole blood hollow fiber filter medium as used in Example 8 d –1, or a reaction of components from the filter media with plasma components occurs because this could falsify the amounts of plasma components determined in the plasma sample after cross-flow filtration.

The coated whole blood hollow fiber membrane filter medium was contacted with a plasma sample of 1 ml for 10 minutes using 5 pieces of 1 cm length each of the coated fiber as performed in Example 5. The plasma sample was gained from whole blood by a conventional centrifugation process. The amount of plasma components (analytes) in the applied plasma sample was then compared to the amount of plasma components (analytes) in the same sample called "reference" which was not contacted with a coated filter medium. The deviation was determined in percent and is shown in Table 12 for Example 8 d –2.

It was also determined, whether certain plasma components are removed upon cross-flow filtration as performed in Examples 6, e.g. due to eventually reduced pore sizes of the coated whole blood hollow fiber membrane filter medium. A coated whole blood hollow fiber membrane filter medium as used in Examples 8 d –1 with filter module properties according to Table 11 have been tested in this respect with an already centrifuged plasma sample.

TABLE 11

| Example | Length of fiber [mm] | Coating product and dilution | 1. Coating procedure 2. Flushing procedure | Volume of applied plasma [ml] | Pump cycles [—] |
|---|---|---|---|---|---|
| 8 d –3 | 77 | F8261 (Evonik) 1:60 | 1. oe 2. oe | 1.4 | 50 |

The amount of plasma components (analytes) in the filtrate and in the retentate samples obtained from an already

TABLE 10

| Example | Length of fiber [mm] | Coating product and dilution | 1. Coating procedure** 2. Flushing procedure** | Volume whole blood [ml] | Volume filtrate [ml] | Pump cycles [—] | Hemolysis* in filtrate | Hemolysis* in retentate |
|---|---|---|---|---|---|---|---|---|
| 8 d-1 | 62 | F8261 (Evonik) 1:60 | 1. oe 2. oe | 1.8 | 0.4 | 50 | o | n |

*o = no hemolysis, n = substantially no hemolysis, m = medium degree of hemolysis, h = high degree of hemolysis
**oe = "open-end" hollow fiber membrane filter during the coating process It can be seen that due to the reduced wettability the flux is reduced and more time or rather more pumping cycles are needed to get a high recovery of plasma. It also can be seen that hemolysis is avoided.

The hollow fiber quality "d" is therefore improved by this coating with a reduced hydrophilicity.

centrifuged plasma by in-out cross-flow filtration as described above was compared to the amount of plasma components (analytes) obtained by the same whole blood "reference" sample without filtration. The analytes in the filtrate represent the molecules which pass through the membrane, the analytes in the retentate indicate if some molecules are retained by the membrane. The deviation was determined in percent referred to the "reference" sample and is shown in Table 12.

TABLE 12

| | | Deviation of concentrations [%] | | |
|---|---|---|---|---|
| | | 8 d −2 10 min contact | 8 d −3 Plasma filtration | |
| Plasma components | | in 1 ml plasma | Filtrate | Retentate |
| Electrolytes | Potassium | 0.00 | 3.17 | −1.59 |
| | Sodium | −0.68 | 2.86 | −1.43 |
| | Calcium | 0.00 | 2.19 | −3.51 |
| | Magnesium | 2.70 | −2.90 | −12.32 |
| | Chloride | −0.93 | 2.80 | −1.87 |
| | Phosphate | −0.78 | −0.99 | −4.46 |
| Lipids | Triglyceride | 2.80 | −2.25 | −7.87 |
| | Cholesterol | −2.26 | 0.77 | −3.08 |
| | HDL cholesterol | 0.00 | 0.00 | −1.89 |
| | LDL cholesterol | −5.33 | 3.39 | −1.69 |
| Infection markers | CRP | 0.61 | 0.00 | −2.59 |
| Enzymes | GOT/AST | 14.29 | 0.00 | 0.00 |
| | Lipase | 4.69 | −3.10 | −5.31 |
| Substrates | Albumin | 0.00 | 2.56 | −2.56 |
| | Bilirubin total | 0.00 | 25.00 | 25.00 |
| | Glucose | −1.35 | 1.43 | −2.14 |
| | Creatinine | 0.00 | 4.00 | −4.00 |
| Proteins | IgG | −15.27 | 0.57 | −3.59 |
| | Ferritin | 3.28 | 2.37 | −0.84 |

— = no value available

The results in Table 12 show only few and low deviations of the plasma for the analytes GOT and IgG obtained after a 10 minute contact with the coated hollow fiber membrane filter media in 8 d −2. The plasma filtration result 8 d −3 shows better results and almost no deviations especially for the plasma filtrate. Only the concentration of bilirubin is changed after the membrane passage from 0.4 mg/dL to 0.5 mg/dL. The indication of this measure has only one position after the decimal point and therefore a slight change in the value leads to high deviation in the percentage indication, and in this case to 25%.

While specific embodiments of the invention have been shown and described in detail to illustrate the inventive principles, it will be understood that the invention may be embodied otherwise without departing from such principles.

What is claimed is:

1. A whole blood hollow fiber membrane filter medium including
a ceramic material having pores of a pore size that ensures permeability to blood plasma or serum, but retains blood cells;
wherein hollow fibers of the whole blood hollow fiber membrane are tubular, having a radially inner surface in an interior of the hollow fiber, wherein the hollow fibers are ceramic hollow fibers
wherein the median pore diameter is in the range of from about 100 nm to about 1500 nm, or from about 150 nm to about 1300 nm, or from about 190 nm to about 1280 nm; and
wherein the whole blood hollow fiber membrane filter medium is coated on the radially inner surface of the surface of the hollow fiber membrane, the radially inner surface carrying at least one type of functional group from the carboxylate groups, and further carrying at least one type of functional groups selected from the group consisting of:
amino groups, silane groups, and any combinations thereof, and is coated with
a coating material further comprising bifunctional silanes with hydrolysable inorganic ethoxysilyl and fluoralkyl chains, or
fluoralkyl functional oligosiloxanes;
wherein the ceramic material comprises one or more ceramic materials selected from the group consisting of alumosilicate, magnesium silicate, and calcium titanate.

2. The whole blood hollow fiber membrane filter medium according to claim 1, wherein
the whole blood hollow fiber membrane filter medium consists of the ceramic material.

3. The whole blood hollow fiber membrane filter medium according to claim 2, wherein
the pore size ensures permeability to blood plasma but retains blood cells.

4. The whole blood hollow fiber membrane filter medium according to claim 1, wherein
the pore size ensures permeability to blood plasma but retains blood cells.

5. The whole blood hollow fiber membrane filter medium according to claim 1, wherein
the pore size ensures permeability to electrolytes, lipid metabolism substances, markers, enzymes, substrates, proteins, pharmaceuticals, and vitamins.

6. The whole blood hollow fiber membrane filter medium according to claim 1, wherein
the whole blood hollow fiber membrane filter medium is a whole blood hollow fiber membrane cross-flow filter medium.

7. The whole blood hollow fiber membrane filter medium according to claim 1, wherein
the whole blood hollow fiber membrane filter medium is a whole blood hollow fiber membrane dead-end filter medium.

8. The whole blood hollow fiber membrane filter medium according to claim 1, wherein
the whole blood hollow fiber membrane filter medium has opposed ends and the opposed ends are open.

9. The whole blood hollow fiber membrane filter medium according to claim 1, wherein
the pore size allows molecules of less than about 8,000 kDa to pass.

10. The whole blood hollow fiber membrane filter medium according to claim 1, wherein
the median pore diameter is in a range of from about 190 nm to about 1,280 nm.

11. The whole blood hollow fiber membrane filter medium according to claim 1, wherein
the pores have a D10 pore diameter that is in a range of from about 150 nm to about 5,000 nm, and
the pores have a D90 pore diameter that is in the range of from about 30 nm to about 1,000 nm.

12. The whole blood hollow fiber membrane filter medium according to claim 1, wherein
the pores have an average pore diameter that is in a range of from about 100 nm to about 1,500 nm.

13. The whole blood hollow fiber membrane filter medium according to claim 1, wherein
the pores have a median pore diameter that is in a range of from about 100 nm to about 1,500 nm, and
wherein the pores have an average pore diameter that is in the range of from about 100 nm to about 1500 nm.

14. The whole blood hollow fiber membrane filter medium according to claim 1, wherein
the ceramic material comprises a silicon carbide.

15. The whole blood hollow fiber membrane filter medium according to claim 1, wherein
the ceramic material further comprises a metal oxide selected from the group consisting of aluminum oxide, silicon oxide, titanium oxide, and any combination thereof.

16. The whole blood hollow fiber membrane filter medium according to claim 1, wherein
the ceramic material further comprises at least one metal oxide selected from the group consisting of zirconium oxide and yttrium oxide.

17. The whole blood hollow fiber membrane filter medium according to claim 1, wherein
the ceramic material further comprises a sintered alpha aluminum oxide.

18. The whole blood hollow fiber membrane filter medium according to claim 17, wherein
the ceramic material further comprises titanium dioxide, wherein the titanium dioxide is present in an amount of 0.1 wt.-% to 0.5 wt.-% based on the total weight of the ceramic material.

19. The whole blood hollow fiber membrane filter medium according to claim 17, wherein
a volumetric medium particle size of the sintered alpha aluminum oxide is from about 0.1 μm to about 2.0 μm.

20. The whole blood hollow fiber membrane filter medium according to claim 19, wherein
the whole blood hollow fiber membrane filter medium has an outer diameter Do of from about 0.4 mm to about 3.0 mm.

21. The whole blood hollow fiber membrane filter medium according to claim 20, wherein
the whole blood hollow fiber membrane filter medium has an inner diameter Di of from about 0.2 mm to about 2.0 mm, provided that the inner diameter Di is smaller than the outer diameter Do.

22. The whole blood hollow fiber membrane filter medium according to claim 21, wherein
a ratio D0/Di of the outer diameter $D_o$ to the inner diameter Di, is in a range of from about 1.3 to about 2.0.

23. The whole blood hollow fiber membrane filter medium according to claim 21, wherein
the outer diameter Do is from about 0.5 mm to about 2.0 mm and the inner diameter Di is from about 0.3 mm to about 1.3 mm.

24. The whole blood hollow fiber membrane filter medium according to claim 1, wherein
the whole blood hollow fiber membrane filter medium has a wall thickness of about 0.1 mm to about 1.0 mm.

25. The whole blood hollow fiber membrane filter medium according to claim 1, wherein
a single hollow fiber membrane of the whole blood hollow fiber membrane filter medium comprises a length 0.5 cm to 8 cm length and a filtration area of from about 3 mm$^2$ to about 500 mm$^2$.

26. The whole blood hollow fiber membrane filter medium according to claim 1, wherein
the whole blood hollow fiber membrane filter medium comprises a porosity from about 30% to about 70%.

27. The whole blood hollow fiber membrane filter medium according to claim 1, wherein
the whole blood hollow fiber membrane filter medium is modified by coating or pre-wetting the whole blood hollow fiber membrane filter medium.

28. The whole blood hollow fiber membrane filter medium according to claim 27, wherein
the whole blood hollow fiber membrane filter medium is pre-wetted with a salt solution, a solution of a blood stabilization agent, or a combination thereof.

29. The whole blood hollow fiber membrane filter medium according to claim 28, wherein
the salt solution is a sodium chloride solution, and wherein the whole blood hollow fiber membrane is not dried after pre-wetting.

30. The whole blood hollow fiber membrane filter medium according to claim 28, wherein
the blood stabilization agent is heparin.

31. The whole blood hollow fiber membrane filter medium according claim 27, wherein
the whole blood hollow fiber membrane filter medium is pre-wetted with a citrate buffer solution.

32. The whole blood hollow fiber membrane filter medium according to claim 1, wherein
the whole blood hollow fiber membrane filter medium is modified so as to have a negative zeta potential.

33. The whole blood hollow fiber membrane filter medium according to claim 1, wherein
the whole blood hollow fiber membrane filter medium is coated a coating material including bifunctional silanes with hydrolysable inorganic ethoxysilyl and fluoroalkyl chains.

34. A method of separating blood plasma/serum from a whole blood sample, the method including the following steps:
providing a whole blood hollow fiber membrane filter medium according to claim 1;
providing a cylindrical filter housing having opposing ends and an opening for filtrate release in a cylindrical wall of the cylindrical filter housing, the opening arranged between the opposing ends of the housing;
embedding opposing ends of the whole blood hollow fiber membrane in a potting/sealing material, potting/sealing the whole blood hollow fiber membrane in an interior of the cylindrical filter housing;
pre-wetting the whole blood hollow fiber membrane filter medium with a citrate buffer solution or an EDTA (ethylenediaminetetraacetic acid) buffer solution;
filtering a whole blood sample with the pre-wet whole blood hollow fiber membrane filter medium so that blood plasma or serum passes through the whole blood hollow fiber membrane filter medium and blood cells are retained.

35. The method according to claim 34, wherein
the blood plasma/serum shows no or substantially no hemolysis.

36. The method according to claim 34, wherein
filtering is carried out by cross-flow filtration.

37. The method according to claim 36, the cross-flow filtration including
passing the whole blood along a longitudinal extension of the whole blood hollow fiber membrane filter medium, optionally alternately in both directions of the longitudinal extension, by applying positive pressure or by applying negative pressure.

38. The method according to claim 37, wherein
the positive pressure is in a range from about 0.5 bar to 1.5 bar and the negative pressure is in a range from about 0.5 bar to about 1.0 bar.

39. The method according to claim 37, the cross-flow filtration being performed as in-out cross-flow filtration or out-in cross-flow filtration.

40. The method according to claim 34, including
diluting the whole blood sample with isotonic sodium chloride solution in a ratio of from 0.5:1 to 1:5.

41. The method according to claim 34, including
stabilizing the whole blood sample with an anti-coagulation agent selected from the group consisting of EDTA, citrate, heparin, and combinations thereof.

42. The method according to claim 34, including
pre-treating the whole blood sample with lectin as a cell agglomeration agent.

43. A method of manufacturing a whole blood hollow fiber filter, the method comprising the steps of:
forming a whole blood hollow fiber membrane filter medium by a phase inversion process from a spinning dope including at least one ceramic powder material, at least one polymer, and at least one solvent;
  wherein the ceramic powder material comprises one or more ceramic materials selected from the group consisting of alumosilicate, magnesium silicate, and calcium titanate;
  wherein the polymer is polyacrylonitrile or polyethersulfone;
  wherein the solvent includes n-methyl-pyrrolidone;
conducting the spinning dope through the annulus cross-section of a nozzle to give a green hollow fiber;
sintering the green hollow fiber at a temperature from about 1,350° C. to about 1,700° C. for a time interval of at least 1 hour to form a ceramic hollow fiber having pores of a pore size that ensures permeability to blood plasma or serum, but retains blood cells, wherein a median pore diameter of the hollow fibers is in the range of from about 100 nm to about 1500 nm, or from about 150 nm to about 1300 nm, or from about 190 nm to about 1280 nm;
applying a coating onto a radially inner surface of the surface of the one or more ceramic hollow fibers, the coating having at least one type of functional group from the carboxylate groups, the coating further including at least one type of functional groups selected from the group consisting of: amino groups, silane groups, and any combinations thereof;
coating the radially inner surface of the surface of the ceramic hollow fibers with a coating material comprising bifunctional silanes with hydrolysable inorganic ethoxysilyl and fluoralkyl chains, or fluoralkyl functional oligosiloxanes;
forming a whole blood hollow fiber membrane from one or more coated ceramic hollow fibers;
providing a cylindrical filter housing having opposing ends and an opening for filtrate release in a cylindrical wall of the cylindrical filter housing, the opening arranged between the opposing ends of the housing;
embedding opposing ends of the whole blood hollow fiber membrane in a potting/sealing material, potting/sealing the whole blood hollow fiber membrane in an interior of the cylindrical filter housing.

* * * * *